(12) United States Patent
Massengale et al.

(10) Patent No.: US 8,672,889 B2
(45) Date of Patent: Mar. 18, 2014

(54) SOFT TISSUE TUNNELING DEVICE

(75) Inventors: Roger Massengale, Mission Viejo, CA (US); Steve Khalaj, Laguna Hills, CA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 389 days.

(21) Appl. No.: 12/146,397

(22) Filed: Jun. 25, 2008

(65) Prior Publication Data

US 2008/0312677 A1  Dec. 18, 2008

Related U.S. Application Data

(63) Continuation-in-part of application No. 11/744,667, filed on May 4, 2007.

(60) Provisional application No. 60/798,238, filed on May 5, 2006.

(51) Int. Cl.
*A61M 5/178* (2006.01)

(52) U.S. Cl.
USPC .................. 604/165.04; 604/164.05

(58) Field of Classification Search
USPC ............... 604/510, 115, 158, 160, 165.01, 604/165.03, 165.04, 22, 104, 46, 161, 171, 604/533, 164.05
See application file for complete search history.

(56) References Cited

U.S. PATENT DOCUMENTS

| 623,022 | A | * | 4/1899 | Johnson | 607/116 |
|---|---|---|---|---|---|
| 4,578,061 | A | | 3/1986 | Lemelson | |
| 4,834,710 | A | * | 5/1989 | Fleck | 604/171 |
| 5,300,032 | A | | 4/1994 | Hibbs et al. | |

(Continued)

FOREIGN PATENT DOCUMENTS

| GB | 2377889 A | 1/2003 |
|---|---|---|
| JP | 2003062068 | 3/2003 |

(Continued)

OTHER PUBLICATIONS

International Search Report for Application No. PCT/US2008/068238 mailed May 8, 2009 (PCT/US2008/068238 is the corresponding PCT application of the present application).

*Primary Examiner* — Aarti B Berdichevsky
*Assistant Examiner* — Brooke Matney
(74) *Attorney, Agent, or Firm* — Dority & Manning, P.A.

(57) ABSTRACT

A tissue tunneling device is configured to be delivered within the body. The tunneling device includes a shaft with a blunt distal end to prevent coring or other damage to tissue during the delivery of the tunneling device. In some arrangements, the shaft includes one or more lumen, through which medication or another fluid may be administered. An anesthetic or other pain relieving medication may be delivered through the lumen to lessen the discomfort of delivering the tunneling device to the desired anatomical site. The handle of the tunneling device can be adapted to receive a syringe or another type of fluid source. The shaft may also include a retractable needle for facilitating the advancement of the tunneling device through skin or other tissue. The shaft may also be provided with an outer sheath, which may be left within the anatomy after the tunneling device has been removed. The tunneling device can be configured to prevent or reduce relative rotation or other movement between the shaft and the sheath. The shaft may be malleable for custom-shaping the tunneling device prior to and/or during delivery.

27 Claims, 18 Drawing Sheets

(56) References Cited

U.S. PATENT DOCUMENTS

| | | |
|---|---|---|
| 5,306,240 A | 4/1994 | Berry |
| 5,391,152 A * | 2/1995 | Patterson ............. 604/165.04 |
| 5,630,802 A | 5/1997 | Moellmann et al. |
| 5,868,729 A | 2/1999 | Pelfrey |
| D449,887 S | 10/2001 | Haberland et al. |
| 6,336,914 B1 | 1/2002 | Gillespie, III |
| 6,368,315 B1 * | 4/2002 | Gillis et al. ............. 604/523 |
| 6,558,353 B2 * | 5/2003 | Zohmann ................ 604/158 |
| 6,589,262 B1 | 7/2003 | Honebrink et al. |
| 6,641,564 B1 | 11/2003 | Kraus |
| 6,645,178 B1 * | 11/2003 | Junker et al. ........... 604/164.05 |
| 6,685,648 B2 | 2/2004 | Flaherty et al. |
| 7,232,425 B2 | 6/2007 | Sorenson et al. |
| 7,264,622 B2 * | 9/2007 | Michelson ............. 606/86 A |
| 7,655,014 B2 * | 2/2010 | Ko et al. ................. 606/129 |
| 2002/0107506 A1 | 8/2002 | McGuckin |
| 2003/0088212 A1 | 5/2003 | Tal |
| 2004/0230204 A1 | 11/2004 | Wortley et al. |
| 2005/0113768 A1 | 5/2005 | Patrickson |
| 2005/0119619 A1 | 6/2005 | Haining |

FOREIGN PATENT DOCUMENTS

| | | |
|---|---|---|
| WO | WO 2006/050191 | 5/2006 |
| WO | WO 2007/114875 | 10/2007 |
| WO | WO 2007/130605 | 11/2007 |

* cited by examiner

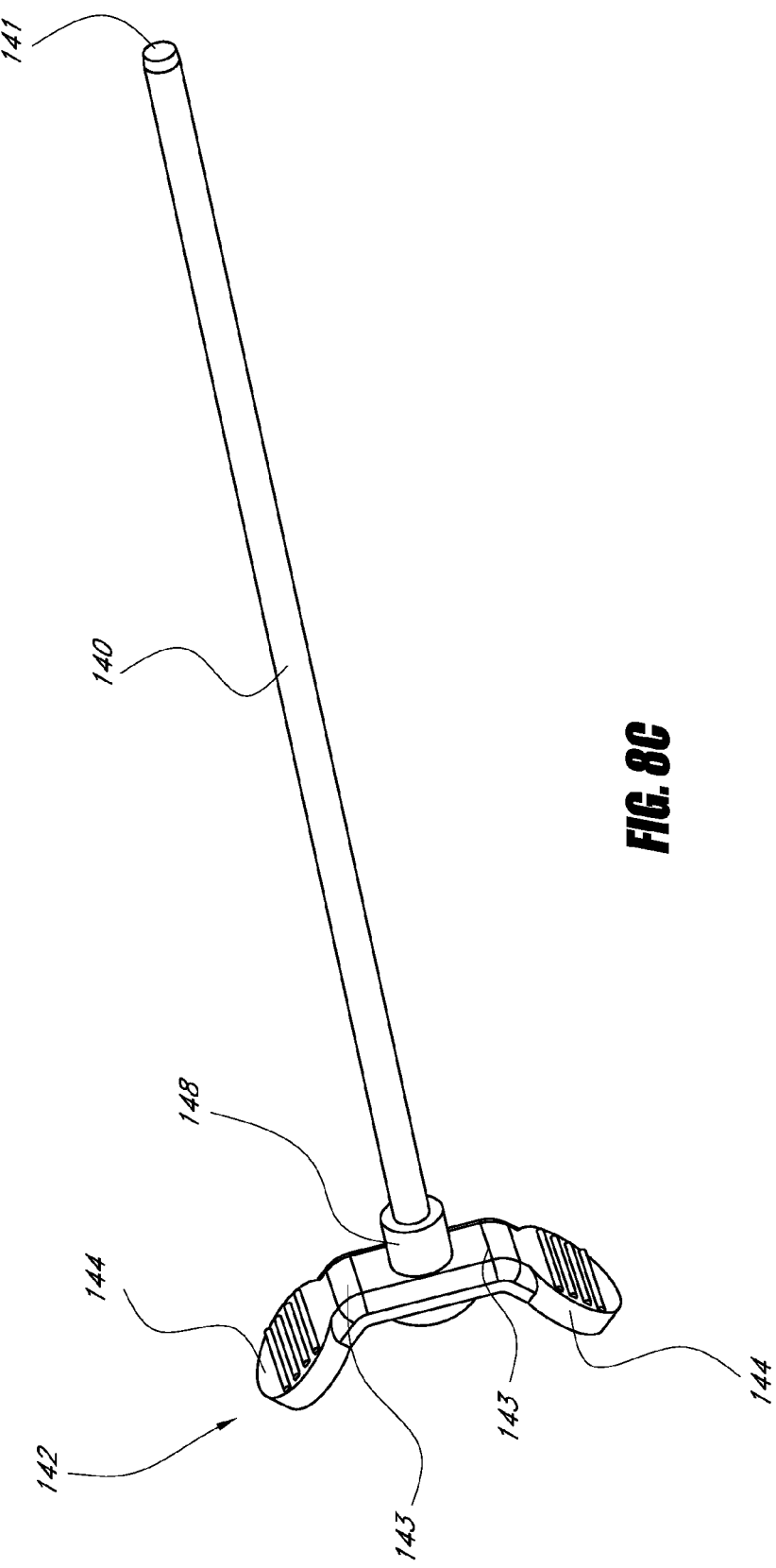

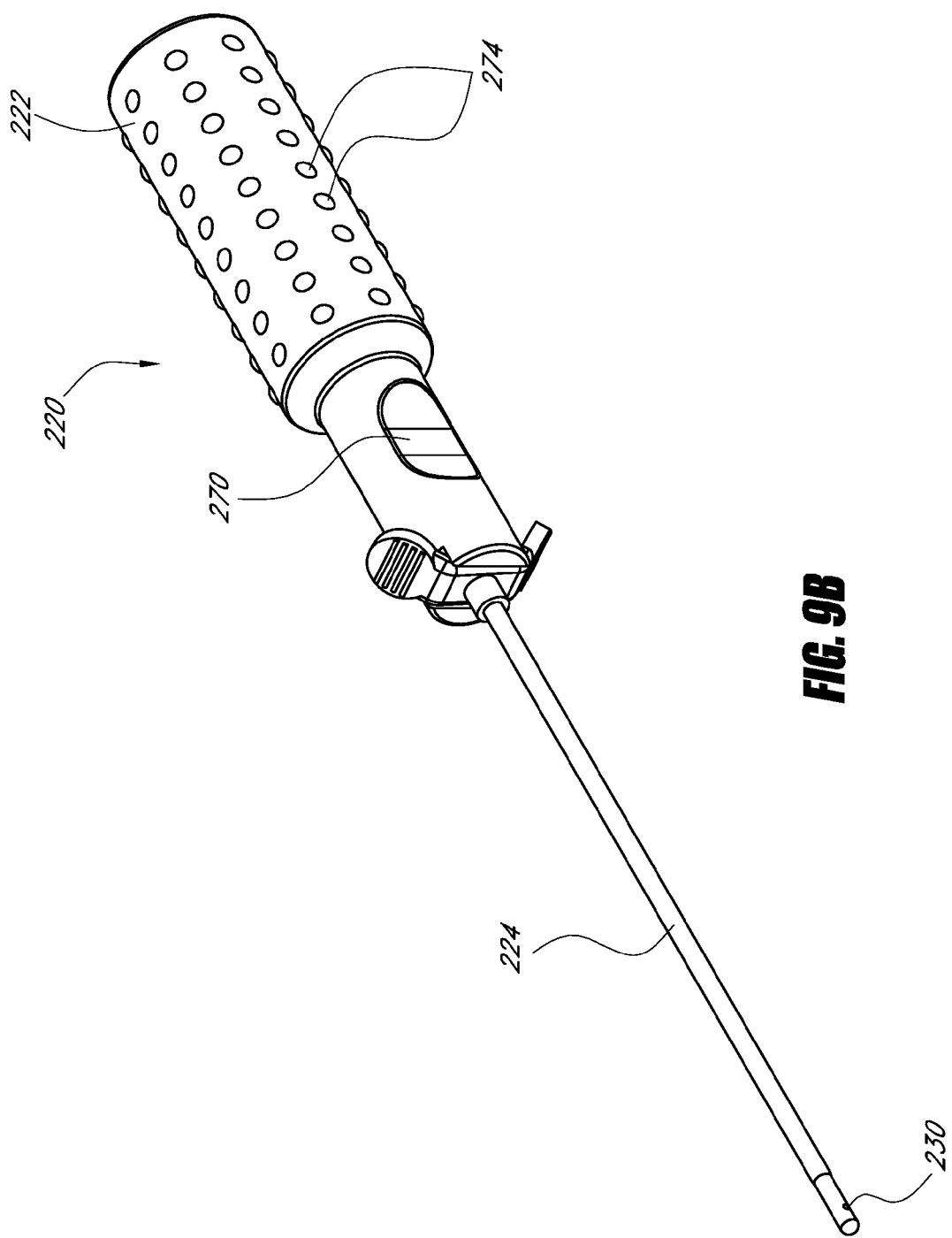

SOFT TISSUE TUNNELING DEVICE

RELATED APPLICATIONS

This application is a continuation-in-part of U.S. patent application Ser. No. 11/744,667, filed May 4, 2007, pending, which claims the priority benefit under 35 U.S.C. §119(e) of U.S. Provisional Application No. 60/798,238, filed May 5, 2006, both of which are hereby incorporated by reference in their entireties.

BACKGROUND OF THE INVENTIONS

1. Field of the Inventions

This invention generally relates to soft tissue tunneling devices and, in particular, to an improved tunneling device for the introduction of a catheter into the body of a patient.

2. Description of the Related Art

Devices used to administer a fluid inside the anatomy are well known. Hypodermic needles, catheters and the like are often used to deliver medication and other fluids to targeted sites within the body. In many instances, catheters are preferred because they can deliver fluid to a particular site over a period of time. However, catheters often require stiff, hollow introducer needles for placement within the anatomy. Typically, such introducer needles have sharp tips that may damage tissue and/or nerves during their delivery into a body. This trauma may also result cause discomfort for the patient.

SUMMARY

A need exists for an improved tunneling device with a blunt distal tip to minimize coring of tissue and other damage associated with advancing an object within the body. The tunneling device may optionally include a retractable needle to assist in puncturing the skin prior to advancing the tunneling device within the patient's body. In addition, a tunneling device with a shapeable malleable shaft will assist in the accurate delivery of the device into the anatomy. Moreover, a tunneling device configured to deliver fluid, anesthetic or other medication to the tissue adjacent the tunneling device will alleviate the discomfort associated with such procedures.

A preferred embodiment involves a tunneling device for creating a subcutaneous path for placement of a catheter in a patient. The tunneling device includes an elongate shaft having a rounded distal end. A handle is secured to the shaft. The handle is configured to permit a user of the tunneling device to manually manipulate the tunneling device.

A preferred embodiment involves a tunneling device for creating a subcutaneous path for placement of a catheter in a patient. The tunneling device includes an elongate shaft having a rounded distal end. A handle is secured to the shaft. The handle is configured to permit a user of the tunneling device to manually manipulate the tunneling device. A sheath (e.g., sheath, IV catheter, angio-catheter, other exterior member, etc.) is positionable over a portion of the shaft. The sheath has a snug fit with the shaft such that the sheath and the shaft can be advanced together within a body of a patient.

A preferred embodiment involves a tunneling device for creating a subcutaneous path for placement of a catheter in a patient. The tunneling device includes an elongate shaft. The shaft has a rounded distal end and defines an interior lumen. A handle is secured to the shaft. The handle is configured to permit a user of the device to manually manipulate the device. At least one fluid exit opening is positioned along the length of the shaft and extends from the interior lumen to an external surface of the shaft. An inlet to the interior lumen to permits liquid to be introduced into the interior lumen and administered to the patient through the at least one fluid exit opening.

A preferred method of introducing a tunneling device into a body involves grasping a handle of a tunneling device, the tunneling device comprising an elongate shaft having a rounded distal end and defining at least one interior lumen and at least one fluid exit opening in fluid communication with the interior lumen. The method also includes introducing the tunneling device into the body of a patient and advancing the tunneling device within the body. Fluid is administered through the interior lumen and into the body of the patient.

A preferred embodiment involves a tunneling device for creating a subcutaneous path for placement of a catheter in a patient. The tunneling device includes an elongate shaft having a rounded distal end. A handle is secured to the shaft and is configured to permit a user of the tunneling device to manually manipulate the tunneling device. The shaft is malleable so as to permit a shape of the shaft to be altered prior to use of the tunneling device.

A preferred embodiment involves a tunneling device for creating a subcutaneous path for placement of a catheter in a patient. The tunneling device includes an elongate shaft having a rounded distal end. A handle is secured to the shaft and is configured to permit a user of the tunneling device to manually manipulate the tunneling device. The shaft is pre-shaped to have a non-linear shape.

One embodiment includes a tunneling device for creating a path for placement of a catheter or other item within an anatomy of a patient. The tunneling device includes an elongated shaft having a generally rounded distal end, a handle secured to said shaft and having a distal end, and a sheath slidably positioned over a portion of said shaft. The handle is configured to permit a user to grasp and manipulate said tunneling device. In some embodiments, the sheath has a generally snug fit with said shaft such that said sheath and said shaft can be advanced together within the anatomy. In other embodiments, the sheath has a generally loose fit relative to said shaft. The distal end of said handle includes a groove that is configured to receive at least a portion of a proximal end of the sheath so as to substantially prevent relative rotation and/or other movement between the shaft and the sheath when the tunneling device is being manipulated within an anatomy.

In some arrangements, the proximal end of said sheath includes a base portion being configured to at least partially fit within the groove of said handle. In one embodiment, the distal end of said handle further includes at least one slot. At least a part of the base portion of the sheath is adapted to be secured within said slot when said sheath is rotated relative to said handle. In other embodiments, the sheath is configured to be selectively removed from the shaft once said tunneling device has been advanced to a desired anatomical location.

According to some embodiments, the shaft includes an interior lumen and at least one opening. Further, the handle includes an interior passageway, said opening and passageway being in fluid communication with said lumen. In one arrangement, the handle includes a fitting configured to place an external fluid source in fluid communication with said passageway and lumen. In other embodiments, the fitting comprises a luer fitting positioned at or near a proximal end of the handle. In other arrangements, the external fluid source comprises a syringe. In yet other embodiments, the shaft is malleable so as to permit a shape of said shaft to be altered prior to use of said tunneling device.

In some embodiments, a tunneling device for creating a path in an anatomy of a patient through which a catheter or another device may be routed is disclosed. The device includes an elongated shaft having an exterior surface and a generally rounded distal end with the defining at least one interior lumen. The device further includes a handle secured to said shaft and one or more fluid openings positioned along said shaft. The handle is configured to permit a user to grasp and manipulate said device. Further, the fluid openings extend from said interior lumen to said external surface of said shaft. The handle includes an internal cavity configured to receive a fluid container, which can be in fluid communication with the interior lumen of the shaft.

According to some embodiments, a method of introducing a tunneling device into a body includes grasping a handle of a tunneling device. The tunneling device includes an elongated shaft having a rounded distal end and defining at least one interior lumen. In addition, the tunneling device includes one or more fluid exit openings that are configured to be in fluid communication with said interior lumen. The method additionally includes positioning a sheath over at least a portion of the elongated shaft of the tunneling device, securing the sheath to the handle of the tunneling device so as to prevent relative rotation between the sheath and the shaft during use of the tunneling device, introducing said tunneling device into the body of a patient, advancing said tunneling device within the body and administering a fluid through said interior lumen and into the body of the patient.

BRIEF DESCRIPTION OF THE DRAWINGS

These and other features, aspects and advantages of the present soft tissue tunneling device are described in detail below with reference to drawings of certain preferred embodiments, which are intended to illustrate, but not to limit, the present inventions. The drawings contain twenty-three (23) figures. It is to be understood that the attached drawings are for the purpose of illustrating concepts of the present inventions and may not be to scale.

FIG. 8C is a perspective view of a sheath configured for placement around the shaft of the tunneling device of FIG. 7.

FIG. 9B is a perspective view of the tunneling device of FIG. 9A comprising a sheath.

DETAILED DESCRIPTION OF THE PREFERRED EMBODIMENTS

Figure 1A:
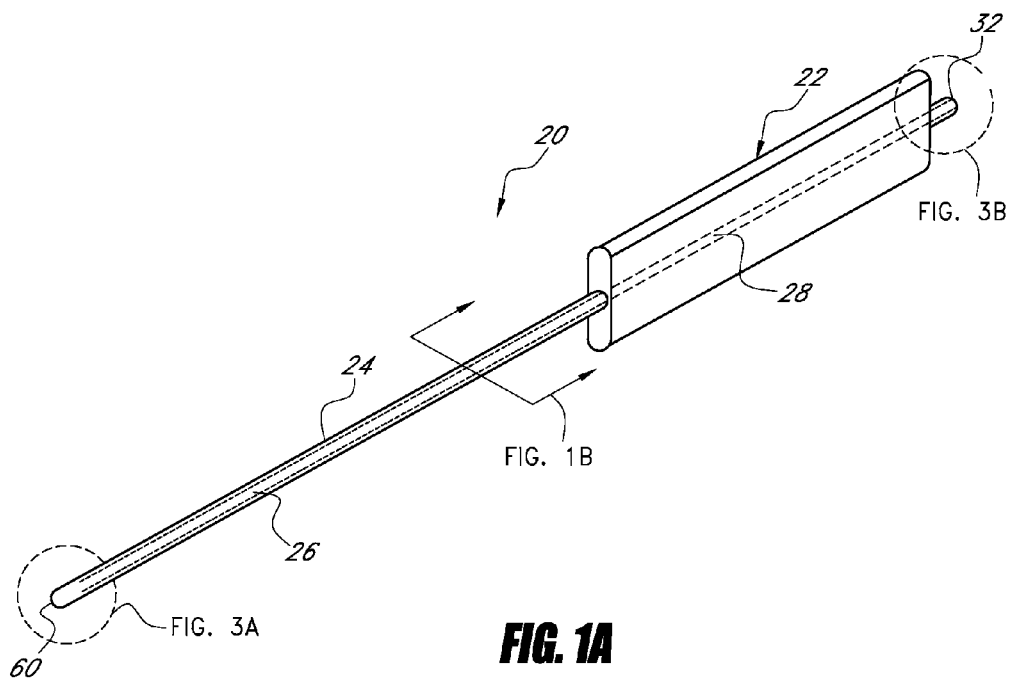
FIG. 1A is a perspective view of a tunneling device having certain features, aspects and advantages of the present invention.

FIG. 1A illustrates a soft tissue tunneling device 20 according to one embodiment of the present invention. The tunneling device 20 preferably includes a handle 22, a shaft 24 and at least one lumen 26 located within the shaft 24. The handle 22 can be constructed of one or more types of plastic or other synthetic or semi-synthetic polymerization product. Alternatively, the handle 22 may be constructed of metal and/or any other suitable material or combination of materials. As illustrated in FIG. 1A, the handle 22 has a generally rectangular shape in cross-section with rounded edges. Preferably, the handle 22 is easy to grip to assist the user in grasping and manipulating the tunneling device 20. The handle 22 can be manufactured with smooth corners and/or other surfaces to reduce any discomfort of handling the tunneling device 20. Further, the handle may have a plurality of molded finger grooves or the like for enhanced gripability. Moreover, a portion or the entire handle 22 may be provided with a non-slip surface. For example, the surface of the handle 22 may be textured or covered with a rubber material.

In one embodiment, the handle 22 is approximately 4 inches long by 1 inch wide by ⅜ inch thick. However, those of skill in the art will appreciate that the length, width and/or thickness of the handle 22 may be greater or lesser than indicated above. In addition, the handle 22 may include one or more knobs, levers, buttons or other control devices to operate any functional aspect of the tunneling device 20 (e.g., retractable needle). As described in greater detail below, the handle 22 can preferably include an interior passageway 28. In some embodiments, the interior passageway 28 is in fluid communication with a luer fitting 32 or other type of connection.

The shaft 24 preferably is constructed of a polymeric material, stainless steel or a combination of both. However, those of skill in the art will appreciate that the handle 22 and the shaft 24 may be constructed of any other suitable material. Further, the shaft 24 of the tunneling device 20 may be configured without a lumen 26.

Figure 3A:
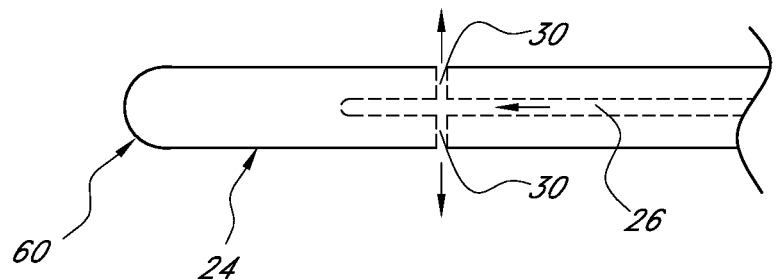
FIG. 3A is a view of a distal end portion of the tunneling device of FIG. 1A with certain features shown in phantom.

In the depicted embodiment, the lumen 26 extends to the distal end of the shaft 24. With reference to the cross-sectional detail in FIG. 3A, the lumen 26 includes at least one, and preferably two outlets 30 that extend to the outside of the shaft 24. The outlets 30 are located near the distal end of the shaft 24 and are oriented opposite of one another (180 degrees apart). However, it will be recognized that the exact number and location of outlets 30 along the length of the shaft 24 may vary. For example, a plurality of openings 30 may be positioned along the entire length of the lumen 26. Alternatively, openings 30 may be situated along one or more portions of the shaft 24 (e.g., the distal end, the middle portion and/or the proximal end). In FIG. 3A, like the lumen 26 to which they are hydraulically connected, the openings 30 preferably have a circular cross-section for more efficient fluid flow. However, the cross-section of the lumen 26 and/or the openings 30 may have any suitable shape. For example, the openings 30 may have a rectangular cross-section with the long end of the opening 30 parallel to the longitudinal end of the shaft 24.

Figure 1B:
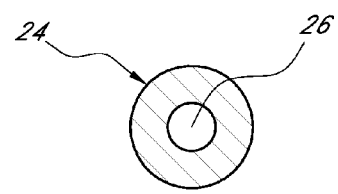
FIG. 1B is a cross-sectional view of the shaft of the tunneling device of FIG. 1A taken along the line labeled FIG. 1B in FIG. 1A.

With continued reference to FIG. 3A, the lumen 26 extends a short distance beyond (e.g., more distal to) the location of the outlets 30. In other embodiments, the lumen 26 may extend even further towards the distal tip of the shaft 24. Alternatively, the lumen 26 may only extend as far as the most distally located outlet 30. In the embodiment depicted in FIG. 1A, the diameter of both the shaft 24 and the lumen 26 remain constant for the entire length of the tunneling device 20. However, the cross sectional shape of the shaft 24 and/or the one or more lumen 26 situated within the shaft 24 may vary along the length of the shaft 24. In one embodiment, the cross-sectional area of the shaft 24 and/or the lumen 26 may decrease with increasing distance from the handle 22. Further, as shown in FIG. 1B, the lumen 26 is concentric to the shaft 24. In other embodiments, the orientation of the lumen 26 within the shaft 24 may be different, especially if the shaft 24 includes two or more lumens 26.

In one embodiment, the shaft 24 is approximately 8 inches long and has an outside diameter of approximately one-eighth of an inch. In another preferred arrangement, the shaft 24 has a diameter of about 0.118 inches. Of course, those of skill in the art recognize that the shaft may be shorter or longer and its diameter may be smaller or larger to satisfy a particular application.

The lumen 26 is preferably in fluid communication with a passageway 28 provided in the handle 22. The combination of the lumen 26 and passageway 28 may be referred to herein generally as a "lumen." In FIG. 1B, the passageway 28 within the handle 22 extends to the proximal end of the handle 22. More preferably, as detailed in FIG. 3B, a luer fitting 32 or other connection device is included at the proximal end of the handle 22. Thus, a fluid delivery device, such as a syringe, a drug delivery pump or the like, may be connected to the luer fitting 32 for the administration of a fluid through the passageway 28, and consequently, to the downstream lumen 26. In an alternative arrangement, a fluid delivery device may be integrated with the tunneling device 20. For example, a fluid delivery device may be integrated with the handle 22 and may provide a mechanism for pressurizing the fluid. The passageway 28 may alternatively terminate on any other suitable portion of the handle 22 (e.g., side surface, proximal end, etc.). In embodiments where the handle 22 is not configured with an inner passageway 28, the lumen 26 exit hole, a luer fitting 32 or other suitable connection device may be included directly on the shaft 24.

Figure 2A:
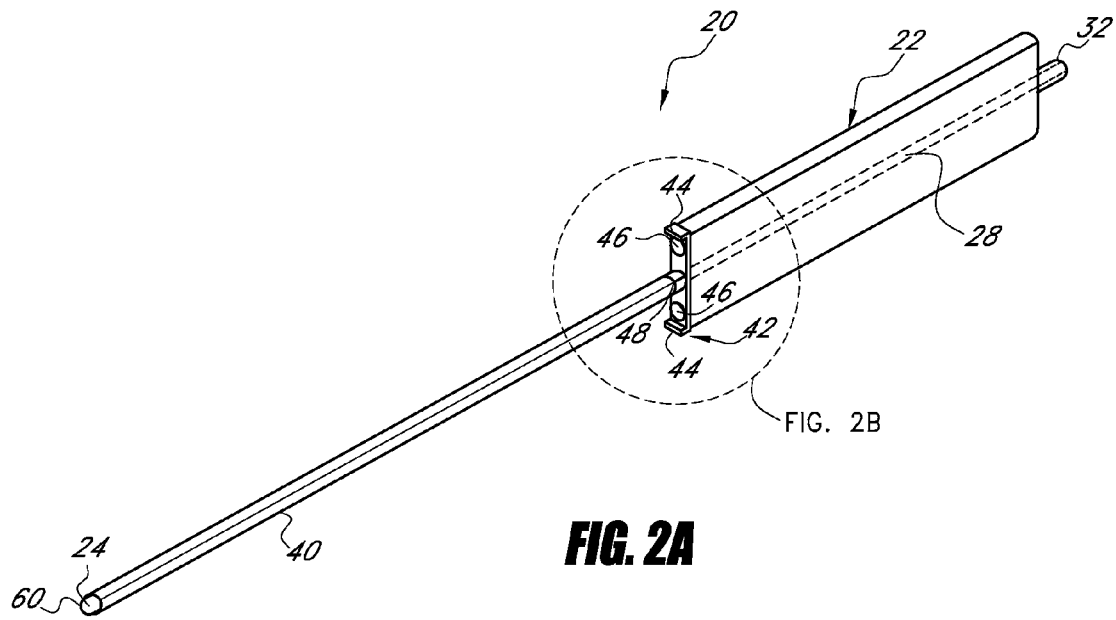
FIG. 2A is a perspective view of the tunneling device of FIG. 1A with a sheath covering a portion of the shaft.

In FIG. 2A, the tunneling device 20 further includes a sheath 40 or other member positioned around the shaft 24. In some embodiments, the sheath 40 comprises polyethylene and/or some other flexible material. However, the sheath 40 may be formed from any of a variety of suitable materials giving due consideration to the goals of flexibility, weight, strength, smoothness, safety, non-reactivity to anatomical systems, etc. Preferably, the inside diameter of the sheath 40 is slightly larger than the outside diameter of the shaft 24, allowing the sheath 40 to fairly easily, but snugly slide over the outer surface of the shaft 24. Preferably, the fit between the shaft 24 and the sheath 40 is such that the pair may be advanced within the body without tissue entering between the shaft 24 and the sheath 40. In some arrangements, the shaft 24 may include a recessed portion to receive the sheath 40. The sheath 40 is configured to cover a substantial majority of the length the shaft 24. In addition, the length of the sheath 40 is preferably selected so as to not cover the one or more outlets 30 of the shaft 24 when the sheath 40 is in its most proximal position on the shaft 24. Thus, in such embodiments, the distal end of the shaft 24 is not covered by the sheath 40 when the sheath 40 is slid against the handle 22.

In some embodiments, the sheath 40 comprises an IV catheter (e.g., angio-catheter) or some other type of catheter. Accordingly, as used herein, the term sheath is a broad term and includes, without limitation, a sheath, catheter, cover and/or any other member that may be positioned along an exterior portion of the shaft. The shape, size (e.g., length, diameter, thickness, etc.) and/or other properties of such a sheath 40 can vary as desired or required by a particular application or use. For example, in some embodiments, a sheath 40 is relatively snug and slidable relative to the shaft 24. Alternatively, a sheath can be loose relative to the adjacent surfaces of the shaft 24.

Figure 2B:
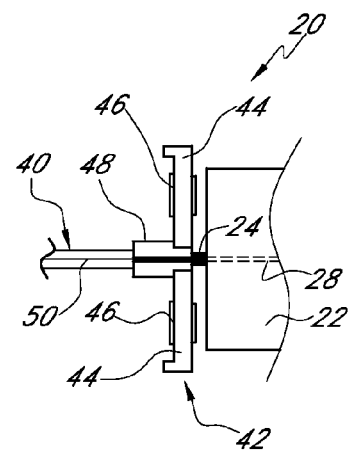
FIG. 2B is a detailed side view of a portion of the tunneling device of FIG. 2A identified by the circle labeled FIG. 2B in FIG. 2A.

In the embodiment illustrated in FIGS. 2A and 2B, the sheath 40 includes a handle portion 42 near its proximal end. The handle portion 42 includes two tabs 44 located opposite of one another. Those of skill in the art will appreciate that the handle portion 42 of the sheath 40 may be configured with more than two tabs 44. As depicted, each tab 44 includes raised contact members 46 on both its distal and proximal sides. The raised contact members 46 may act to restrict the movement of the sheath 40 relative to an adjacent object (e.g., the handle 22, a patient's skin, etc.) and facilitates grasping of the tabs 44. The sheath 40 also includes a hub 48 that connects the tabs 44 to the main distal portion of the sheath 40. As illustrated in FIG. 2B, the sheath 40, including the hub 48, may be configured with a seam 50 along its longitudinal axis. Preferably, the sheath 40 includes at least two parallel seams 50, one on each side of the sheath 40. In other embodiments, more a sheath 40 may be configured with more than two seams 50. As will be discussed in greater detail below, the seams 50 make it easier for a user to peel apart the sheath 40 after the catheter has been positioned within the anatomy. In the depicted embodiment, a user splits the sheath 40 along the one or more seams 50 by pulling apart the tabs 44 of the handle portion 42. Consequently, this facilitates removal of the sheath 40 when one or more objects are situated within the sheath 40 (e.g., a catheter, an instrument, etc.). The seams 50 preferably extend to the distal end of the sheath 40.

Preferably, the shaft 24 of the tunneling device 20A has a blunt distal end 60, as shown in FIGS. 1A and 2A. The blunt distal end 60 helps minimize or eliminate the coring of tissue as the tunneling device 20 is advanced through the anatomy. Further, the blunt distal end 60 inhibits or eliminates damage to nerves and other sensitive tissues. In the depicted embodiments, the blunt distal end 60 is generally rounded and, more particularly, substantially spherical and is the same diameter as the shaft 24. However, any suitable blunt (non-sharp) shape can be used.

Figure 4A:
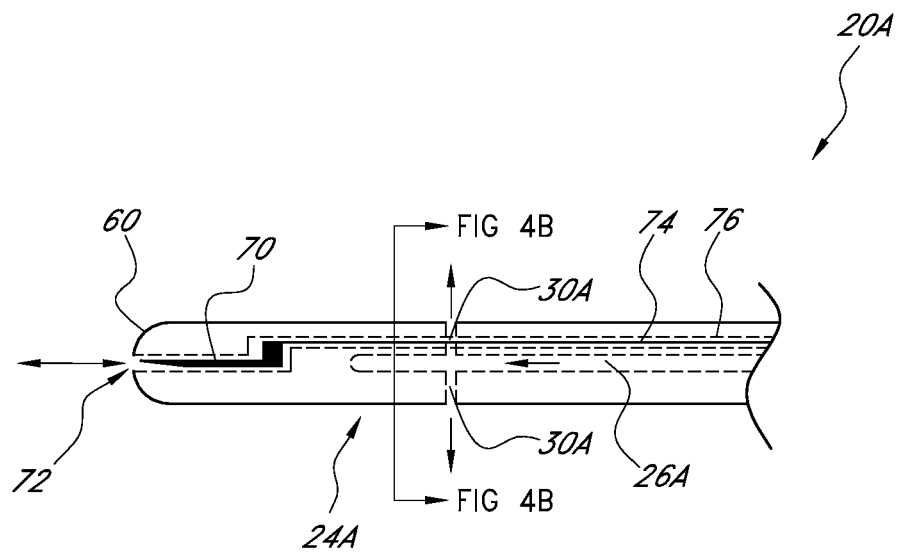
FIG. 4A is a view of a proximal end of a tunneling device according to another embodiment with certain features shown in phantom.
Figure 4B:
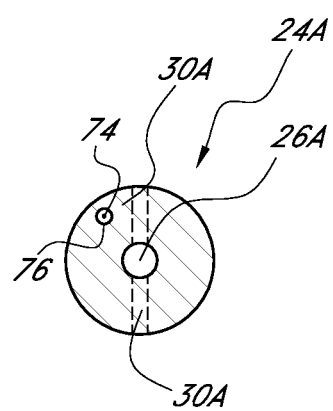
FIG. 4B is a cross-sectional view of the tunneling device of FIG. 4A, taken along the line labeled FIG. 4B in FIG. 4A.

FIG. 4A illustrates a cross-sectional longitudinal view of a shaft 24A according to another embodiment of the tunneling device 20A. The shaft 24A includes a retractable needle 70 that may be used to penetrate the skin, thus, facilitating the introduction of the tunneling device 20 into the anatomy.

Preferably, the retractable needle 70 is housed within the distal end of a needle lumen 76, and may be fully retracted within the needle lumen 76 so that the shaft 24A maintains a substantially blunt distal end 60. The position of the retractable needle 70 within the needle lumen 76 may be changed using any suitable method. For example, in FIG. 4A, the position of the needle 70 is controlled by axially moving a rod 74 that is coupled to the needle 70. In other embodiments, a wire or other suitable member may be used in lieu of a rod 74. As depicted, the rod 74 is housed within the needle lumen 76 of the shaft 24A. Preferably, the rod 74 and the corresponding needle lumen 76 extend proximally to the handle 22 of the tunneling device 20A to permit a user to easily control the position of the retractable needle 70 by hand or by using a control member or other device (not shown). Non-limiting examples of suitable control members include knobs, levers, etc. Alternatively, the rod 74 or other suitable member for controlling the position of the retractable needle 70 may be positioned within the fluid delivery lumen 26.

Regardless of how the needle 70 is manipulated between forward and retracted positions, the shaft 24A may optionally include one or more lumens 26A and/or openings 30A hydraulically connected to such lumen 26A. Preferably, the opening 72 through which the tip of the needle 70 can pass is relatively small in comparison to the total cross-sectional area of the blunt distal end 60 so that the surface on the blunt distal end 60 of the shaft 24A is as smooth and continuous as practicable. In other embodiments, the shaft 24A may include a membrane or other suitable covering when the needle 70 is in the retracted position to create a smoother surface on the blunt distal end 60. Further, the opening 72 may have any suitable shape, size and overall orientation. In the embodiment shown in FIG. 4A, the opening 72 is substantially circular and is concentric with the shaft 24A. Moreover, in an alternative arrangement, the needle 70 may be positioned within the lumen 26A through which fluid is also delivered from the tunneling device 20A, as described below.

Preferably, one or more openings 30A hydraulically connected to a lumen 26A of the shaft 24A are located near the retractable needle 70. Such an arrangement allows an anesthetic or other fluid to be delivered near the site of the needle penetration. In one embodiment, the opening 72 for the needle 70 is itself hydraulically connected to the lumen 26A, further facilitating delivery of anesthetic or other fluid to the area proximate the needle 70.

Figure 5:
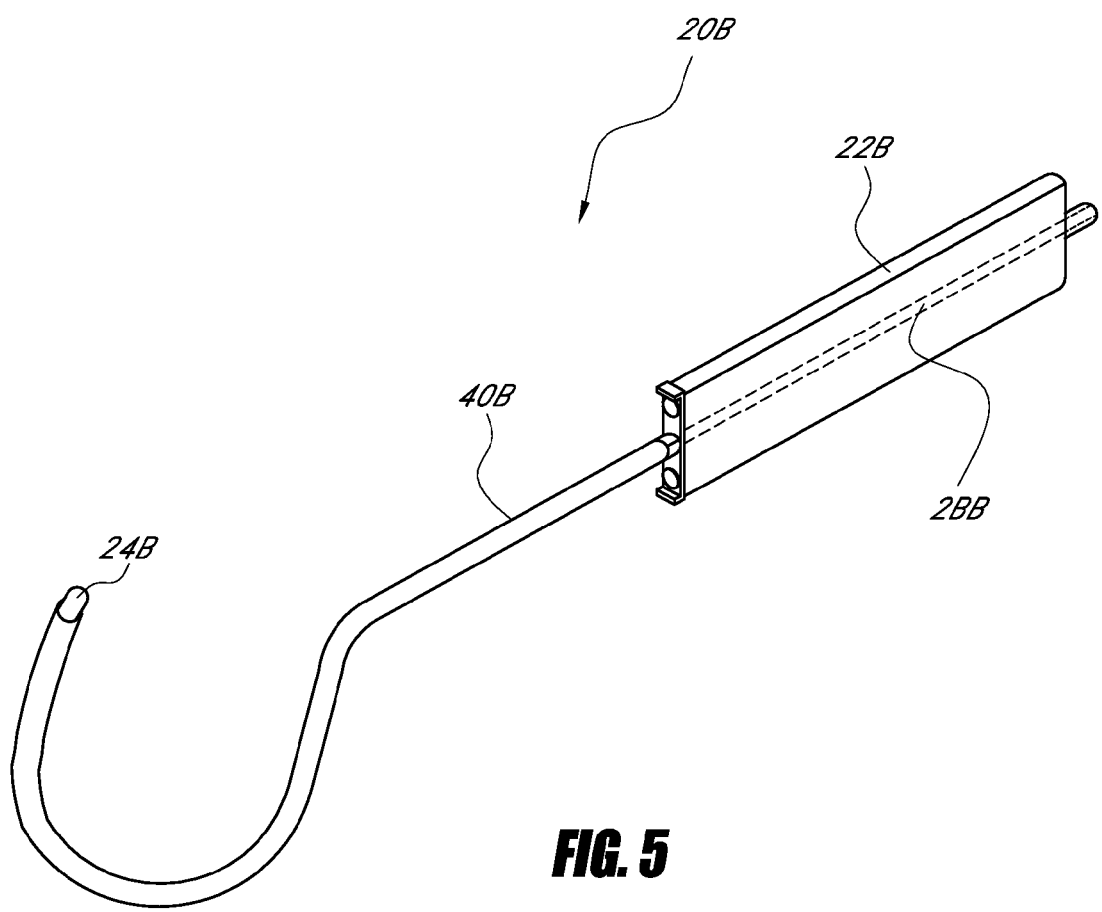
FIG. 5 is a perspective view of a tunneling device according to yet another embodiment.
Figure 6:
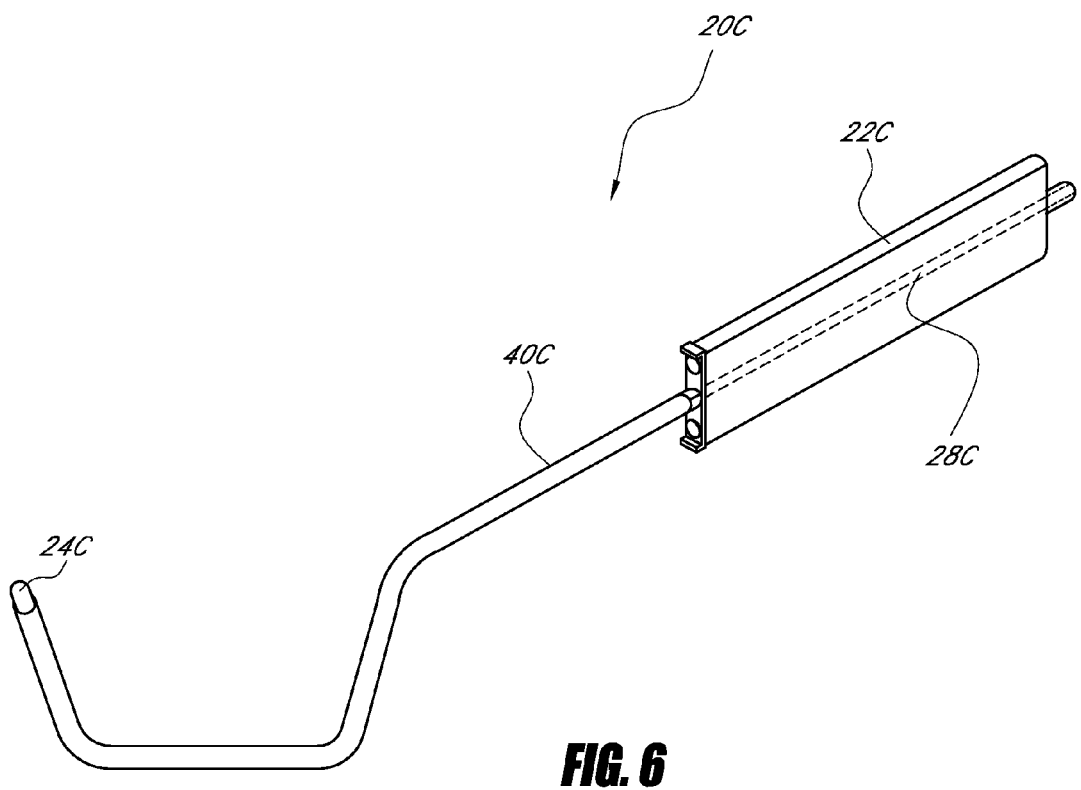
FIG. 6 is a perspective view of a tunneling device according to still another embodiment.

With regard to all the embodiments discussed herein, the shaft of the tunneling device may be manufactured from a malleable material, such as malleable stainless steel. A malleable shaft permits a user to customize the shape of the tunneling device prior to and/or during insertion of the tunneling device into the anatomy. In FIG. 5, the shaft 24B has been bent into a non-linear two-dimensional shape, e.g., a hook shape. The shape of the malleable shaft 24 may be more or less intricate, as may be required by a particular procedure. For example, FIG. 6 depicts a further embodiment of the tunneling device 20C, having a shaft 24C bent into a more convoluted, three-dimensional shape. In such embodiments, the shaft may be formed from a variety of materials, giving due consideration to the goals of malleability, strength, safety and other factors. For example, a stiffer shaft may be desired if a tunneling device is shaped prior to insertion into the anatomy, such as during the manufacturing process. This will better preserve the pre-shaped form of the shaft as the tunneling device is advanced into the anatomy. Alternatively, a more malleable material may be preferred if the shaft will be shaped immediately prior to the delivery of the tunneling device within the anatomy, such as by the user performing the tunneling procedure. Regardless, the tunneling device is preferably configured to prevent the collapse of any interior lumen and any other opening situated inside the shaft. This ensures that the various features of the tunneling device (e.g., fluid delivery through the shaft, the retractable needle, etc.) function properly. For example, if an inner lumen of the shaft collapses or is otherwise obstructed, the administration of fluid to the one or more outlets of the shaft may not be possible.

With continued reference to FIG. 2A, the tunneling device 20 is introduced into the anatomy with the intent to reach a particular location. The tunneling device 20 may be used to aid in the subsequent placement of a catheter or other device. Alternatively, the tunneling device 20 may be used for the direct delivery of a fluid to a targeted site within the anatomy. In use, typically, the tunneling device 20 must first penetrate the skin. In a preferred embodiment, the tunneling device 20 comprises a sharp retractable needle 70 at the distal end of the shaft 24 for piercing the skin (FIG. 4A). Once the skin has been penetrated, the retractable needle 70 is withdrawn into its opening 72, and the shaft 24 of the tunneling device is pushed towards the target area within the anatomy. As depicted in FIG. 4A, the axial position of the needle 70 may be controlled by manipulating a rod 74 that is coupled to the needle 70. Alternatively, a wire or other suitable member may be use in lieu of the rod 74. The rod 74 or other member is situated within lumen 76 of the shaft 24A, and preferably extends to the handle of the tunneling device 20A. The position of the rod 74 or other member (and thus, the position of the needle) may be controlled by hand or by a control member (e.g., knob, lever, etc.) that may be advantageously located on or near the handle. Those of skill in the art will recognize that any other suitable method of controlling the position of the needle 70 can be used. This allows the person using the tunneling device 20A to easily control the position of the needle 74 during all stages of the tunneling procedure.

Once the tunneling device 20 has been inserted under the skin, it is directed, usually between the skin and muscle tissue, to the target region within the body. Preferably, the distal end of the shaft 24 is blunt in order to inhibit damage to sensitive tissues such as nerves. For example, the blunt distal end minimizes coring of tissue as the tunneling device 20 is moved through the anatomy. For example, as illustrated in FIGS. 1A and 2A, the shape of the distal end 60 of the shaft 24 is rounded. After the tunneling device 20 has been inserted under the skin, it may be desirable or necessary to once again penetrate obstructive tissue using the retractable needle 70. Therefore, if the need arises, the needle 70 may be directed distally out of the opening 72 to protrude from the distal end 60 of the shaft 24A. Once the needle 70 has adequately penetrated the target tissue, it may be retracted, permitting the blunt distal end 60 of the shaft 24A to guide the tunneling device 20A through the adjacent anatomical tissue.

Preferably, the shaft 24 includes one or more lumens 26, through which fluid can be administered as the tunneling device 20 is being introduced and delivered to its target site. For example, one or more pain relieving medications, e.g., local anesthetic, may be fed into the lumen 26 to alleviate the pain associated with the tissue tunneling process. In some embodiments, the pain relieving medication or other fluid is delivered to the distal portion of the shaft 24 through one or more outlets 30 (FIG. 3A). Alternatively, as described above, the lumen 26 may be configured with additional outlets 30 positioned at various locations along the length of the shaft 24 to deliver the medication or other fluid to a greater extent of the anatomy. More preferably, the medication or other fluid is intermittently or constantly fed into the lumen to relieve pain throughout the entire tunneling procedure.

Figure 3B:
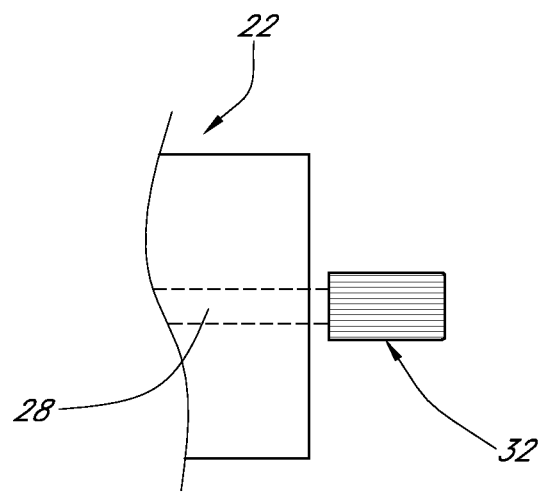
FIG. 3B is a detailed side view of a portion of the handle of the tunneling device of FIG. 1A.

Preferably, a connection fitting (e.g., a luer fitting 32) is positioned at the proximal end of the tunneling device 20 for facilitating the introduction of a fluid through the lumen 26 of the shaft 24. In FIGS. 1A and 3B, the connection fitting is a standard luer fitting 32 and is positioned at the proximal end of the handle 22 of the tunneling device 20. In order to convey fluid through the one or more lumens 26 to the openings 30 of the shaft 24, the user connects the fluid source (e.g., syringe, drug delivery pump, other device, etc.) to the luer fitting 32 and administers the fluid using any suitable method (e.g., actuating the syringe, activating an electric pump, operating a hand pump device, etc.). The user can preferably able to control when and how much fluid is administered through the tunneling device 20, taking into consideration the anticipated level of discomfort, dosage and other factors. The user may also change the fluid source during or after delivery of the tunneling device. Thus, the lumen 26 of the shaft 24 may include a check valve or another suitable flow control device to prevent blood or other bodily fluid from unintentionally flowing proximally through the lumen 26.

Typically, after the tunneling device 20 is advanced to a target location within the anatomy, the tunneling device 20 is removed for the subsequent delivery of one or more catheters, instruments or other item. In one embodiment, a catheter is delivered through the passageway created by the tunneling device 20. Alternatively, the catheter or other item may be delivered through a sheath 40 which was delivered simultaneously with the tunneling device 20 into the anatomy as described above. In such arrangements, the sheath 40 may be subsequently retracted from the anatomy while leaving the catheter or other item in place within the anatomy. Preferably, as discussed above and illustrated in FIG. 2B, the sheath 40 includes one or more seams 50 that facilitate removal of the sheath 40 after it has been withdrawn from the anatomy.

In addition, the tunneling device 20 may be used to facilitate other medical treatment functions. For example, the user may deliver an antibiotic or other medication within the anatomy through the one or more lumen 26 positioned within the shaft 24. Alternatively, the user may withdraw a fluid from the anatomy by introducing a vacuum through the lumen 26. This is especially useful for draining an undesirable fluid from an organ, cyst or other part of the anatomy. In other embodiments, the lumen 26 may be used to withdraw a tissue sample (e.g., biopsy) or other item or substance from the anatomy.

As discussed, the sheath 40 positioned along the exterior of the shaft 24 can comprise a catheter (e.g., IV catheter, angiocatheter) or any other item. For example, an IV catheter can be placed over the shaft 24 for delivery within the anatomy. In some embodiments, once the shaft 24 has been advanced to a desired anatomical location, the shaft can be separated from the IV catheter, sheath or other exterior member. Consequently, an IV catheter or other sheath can remain within the anatomy. Such catheters or other items can be used to transfer fluids to and/or from a particular anatomical location (e.g., to permit the delivery or drainage of fluids, the aspiration or injection of fluids, etc.). Further, as discussed, such catheters can create a pathway through which instruments, devices and/or the like can be inserted or removed.

As discussed above with reference to the embodiments illustrated in FIGS. 5 and 6, the tunneling device may include a malleable shaft that can be shaped before and/or during delivery. Alternatively, a more rigid, pre-formed shaft can be preferably used that will retain its shape during the tunneling procedure. Depending on the particular procedure for which the tunneling is used, the depth and location of the targeted anatomical site, the malleability and other material properties of the shaft, the length of the tunneling device and other factors, the user may optionally shape the shaft during the tunneling procedure. Preferably, a user shapes the tunneling device by exerting a bending force directly on the shaft. In other embodiments, a tool or other device may be used to shape the shaft. The lumen and other openings within the shaft are configured to retain their integrity during the shaping of the tunneling device. Thus, the ability to direct one or more fluids through the shaft preferably is maintained at all times.

As illustrated in FIG. 2A, the tunneling device 20 may include a sheath 40 that is slidably positioned on the outside of the shaft 24. A tunneling device 20 with an outer sheath 40 may be delivered into the human anatomy as described above. Once delivered to the desired anatomical site, the tunneling device 20 can be withdrawn, leaving the sheath within the anatomy. In FIG. 2A, the sheath 40 includes a handle portion 42 that can be manipulated to maintain the sheath 40 within the anatomy as the tunneling device 20 is withdrawn. Preferably, the sheath 40 is configured to maintain its structural integrity after the shaft 24 has been retracted. After the shaft 24 has been retracted, the sheath 40 can be used as a conduit to introduce a fluid (e.g., medication), a medical device, a catheter or other item sized to fit within the sheath 40. The inner wall of the sheath 40 is preferably smooth to facilitate the delivery of another object.

The sheath 40 can be removed by directly retracting it from the anatomy. However, depending on what has been placed within the sheath 40 after removal of the tunneling device 20, it may not be easy, or even possible, to directly pull the sheath 40 out of the body. For example, a catheter or another medical device may have has been inserted within the sheath 40, and it is desirable to maintain such item with the anatomy while removing the sheath 40. Consequently, the sheath 40 can be configured with one or more longitudinal seams 50 (FIG. 2B) that permit the sheath 40 to be split into two or more pieces. In FIG. 2B, the sheath 40 includes two longitudinal seams, positioned opposite of one another. By separating the tabs 44 of the handle portion 42, the sheath 40 splits into two pieces, making it easier to remove the sheath 40 from a catheter or other object situated within the sheath 40. Typically, a catheter includes a luer fitting or similar feature near its proximal end that prevents an outer sheath 40 to be slidably separated from the catheter. Thus, the sheath 40 is advantageously configured with one or more seams so that it may be split into separate sections as it is being withdrawn or after it has been withdrawn. As illustrated in FIGS. 5 and 6, a sheath 40 may be optionally used on a tunneling device with a malleable shaft.

Figure 7:
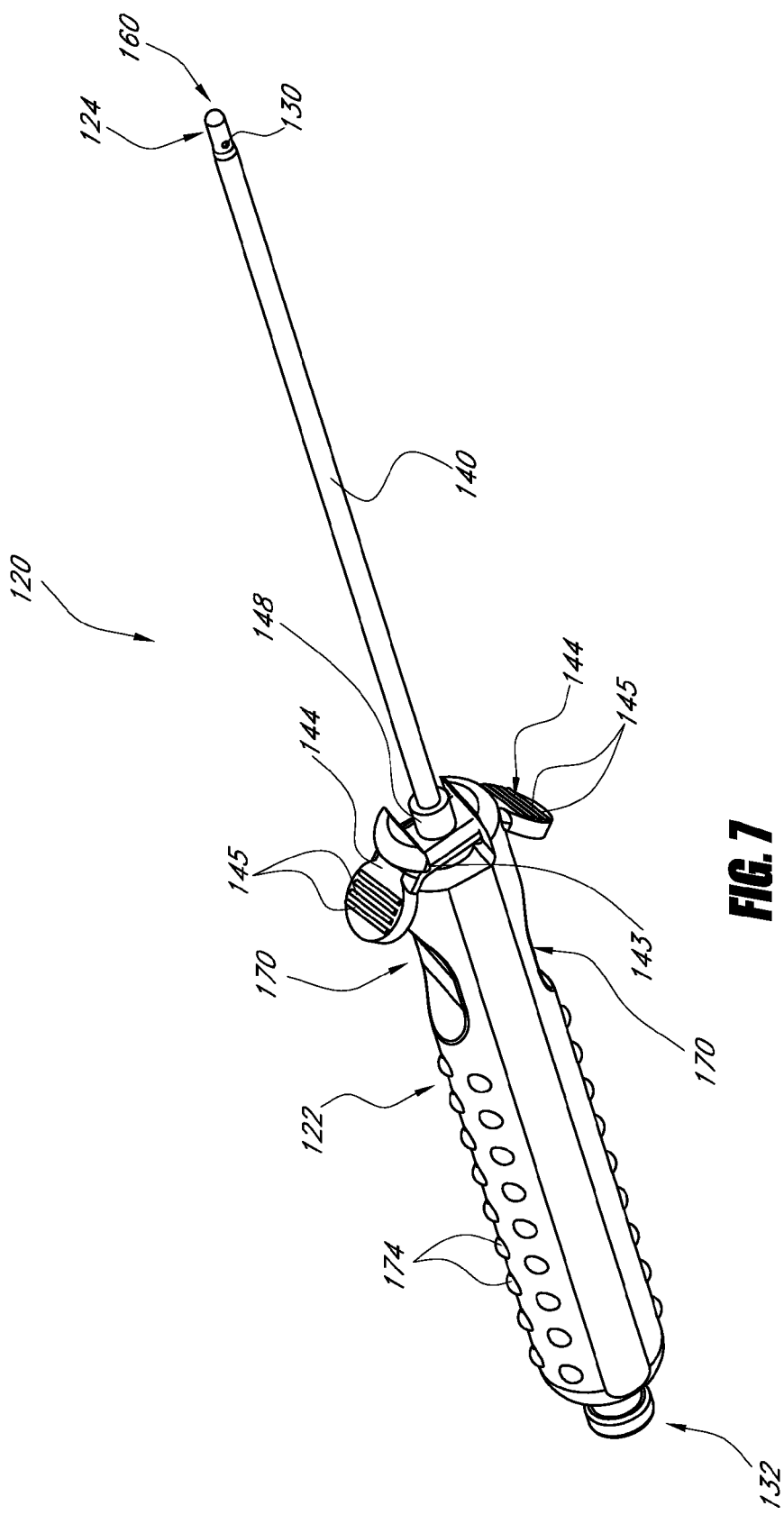
FIG. 7 is a perspective view of a tunneling device according to another embodiment.

FIG. 7 illustrates a perspective view of another embodiment of a tunneling device 120 configured for placement within the anatomy as described herein. As shown, the tunneling device 120 can include a handle 122 and a shaft 124 adapted to slidably receive a removable sheath 140. In addition, the shaft 124 can comprise an internal lumen (not shown) that is in fluid communication with one or more openings 130 situated near the distal end 160 and/or any other location of the shaft 124. Further, the lumen of the shaft 124 can be adapted to be in fluid communication with a passageway (not shown) situated within an internal portion of the handle 122. In some arrangements, fluids and/or other substances are delivered into and/or removed from such a passageway using a luer fitting 132 or other type of standard or non-standard connection.

Figure 8A:
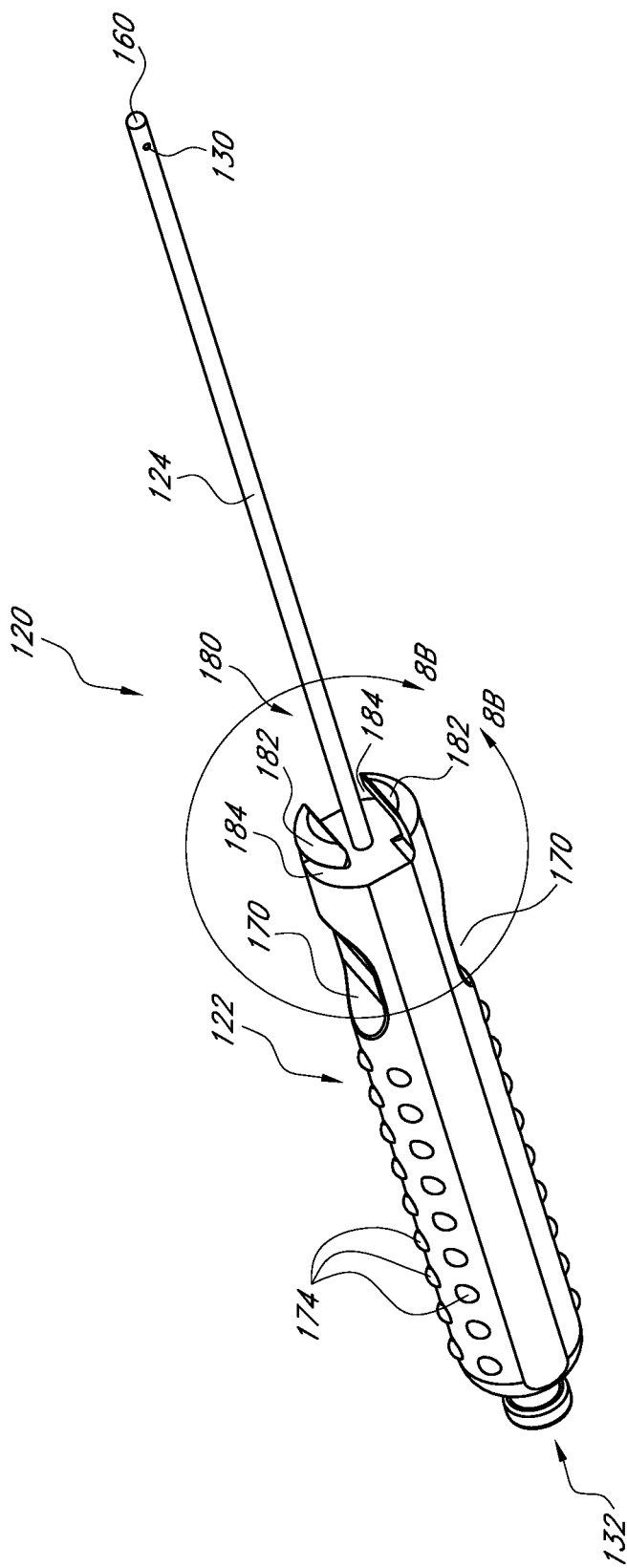
FIG. 8A is a perspective view of the tunneling device of FIG. 7 with the sheath removed from the shaft.
Figure 8B:
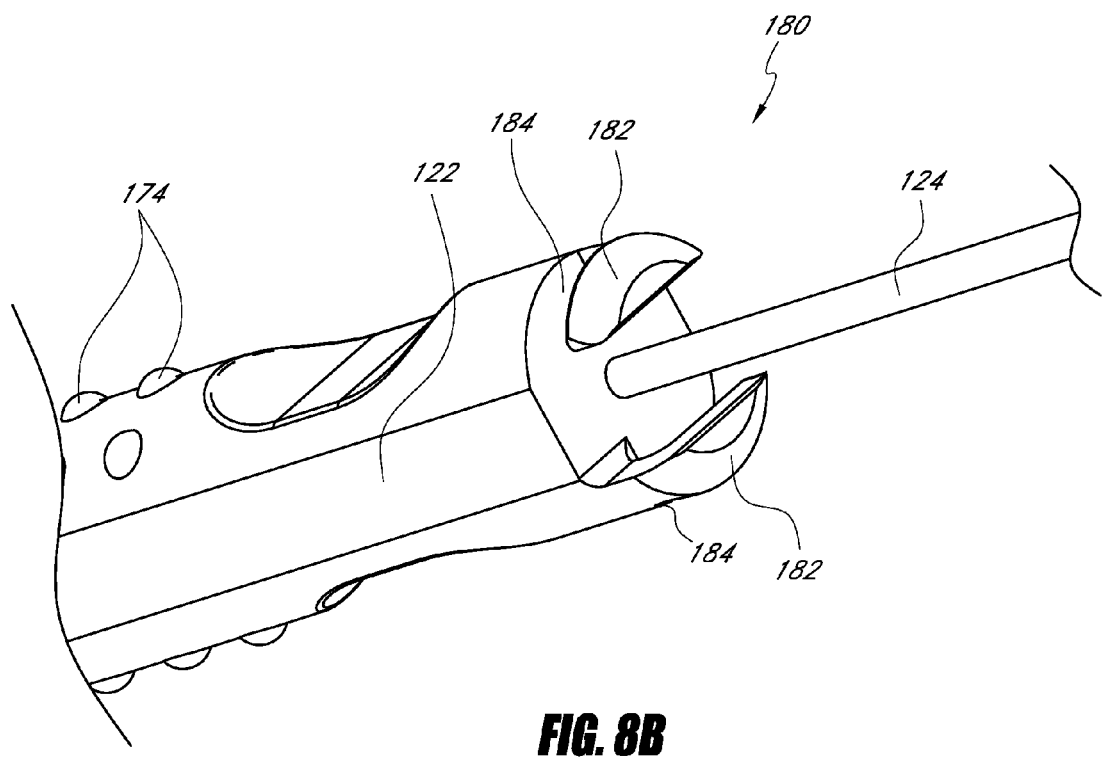
FIG. 8B is a detailed perspective view of the tunneling device of FIGS. 7 and 8A.

Perspective views of the tunneling device 120 of FIG. 7 with the sheath 140 removed from the shaft 124 are illustrated in FIGS. 8A and 8B. In addition, one embodiment of an outer sheath 140 that is adapted to be positioned on the outside of the shaft 124 is depicted in FIG. 8C. With reference to FIG. 8A, the tunneling device 120 can include a handle 122 that is shaped, sized and otherwise configured to be easily grasped and manipulated by a user during a soft tissue tunneling procedure. For example, the handle 122 can comprise a plurality of bumps 174, recesses or other members or features along its exterior surface that enhance the device's tactile properties. In addition, the handle 122 may include one or more grooves 170 that are shaped, sized and positioned to advantageously receive a user's thumb and/or other fingers during use.

As illustrated in FIGS. 7 and 8C, a base portion 142 of the sheath 140 can include one or more tab members 144 that are generally connected to a hub 148 or other common member at or near the proximal end of the sheath 140. The tab members 144, which may include any linear and/or non-linear shape, can be sized and shaped to facilitate handling by a user. For example, in the depicted arrangement, the base portion 142 includes a total of two generally circular tab members 144 that extend outwardly and proximally from the common hub 148. However, the quantity, shape, size, orientation and/or other properties of the base portion 142 and its components can vary as desired or required. As discussed herein with respect to other embodiments, the sheath 140 can include one or more longitudinal seams (not shown in FIGS. 7 and 8C) or other features that can facilitate the splitting and removal of the sheath 140 from a catheter (not shown) that is delivered to a target anatomical location through the intact sheath 140 with the shaft 124 removed, as described previously. As shown, the sheath 140 can include an opening 141 at its distal end through which the tip or distal portion 160 of the shaft 124 may pass (FIG. 8A).

In some arrangements, it is desirable to generally prevent rotation of the sheath 140 relative to the shaft 124, especially once the tunneling device 120 is inserted into the anatomy. This can provide improved control at the handle 122-shaft 124 interface of a tunneling device 120, as the tab members 142 and/or other components or features of the base portion 142 will not interfere with a user's manipulation of the handle 122. In addition, rotational movement of the sheath 140 may assist in advancing or retracting the tunneling device 120 within soft tissue of a patient. Thus, in some arrangements, it may be desirable to substantially fix the sheath 140 for rotation with the shaft 124. Accordingly, the distal end of the handle 122 can include a groove 180 or other engagement feature that is configured to at least temporarily receive and secure one or more areas of the sheath 140, such as, for example, the sheath's base portion 142. As illustrated in the detailed view of FIG. 8B, the groove 180 can comprise a rectangular shape and can generally extend across one or more distal portions of the handle 122. Further, the groove 180 is preferably sized, shaped and otherwise oriented to receive the base portion 142 of the sheath 140. In other embodiments, however, the shape, size and/or other details of the groove 180 or other securement area can vary, as desired or required.

With continued reference to FIGS. 8A and 8B, the groove 180 or other recessed area configured to securely receive a portion of the sheath 140 can be at least partially formed by one or more protruding members 182 located at the distal end of the handle 122. In some embodiments, the protruding members 182 form a unitary structure with the handle 122. Alternatively, the protruding members 182 can be separate items that are joined to the handle 122 using one or more attachment methods or devices, such as, for example, adhesives, fasteners, welds and/or the like. In the illustrated embodiment, the handle 122 comprises two protruding members 182 located on opposite ends of the groove 180. As shown, each of the protruding members 182 generally forms a slot 184 that can be used to secure one or more portions of a removable sheath 140 (e.g., the sheath's base portion 142), as discussed in greater detail herein.

With continued reference to the tunneling device 120 of FIGS. 7 and 8A-8C, the base portion 142 of the sheath 140 can be shaped, sized and otherwise configured to fit within the groove 180 of the handle 122. For example, in some embodiments, a main section 143 of the base portion 142 is designed to fit within the groove 180. As illustrated in FIG. 7, once the base portion 142 of the sheath 140 has been properly aligned and inserted within the groove 180 of the handle 122, the sheath 140 can be rotated relative to the protruding members 182 (e.g., in a counterclockwise direction) in order to secure the base portion 142 within the slots 184. In some arrangements, the protruding members 182 and the corresponding slots 184 are sized, shaped and otherwise configured to secure the base portion 142 therein using a quarter-revolution (e.g., 90°) turn. However, in other embodiments, a greater or lesser degree of relative rotation between the base portion 142 and the handle 122 may be required to temporarily secure or lock the base portion 142 of the sheath 140 to the handle 122 of the device 120. Alternatively, one or more other methods or devices of securing the sheath 140 to the handle 122 of a tunneling device 120 can be used to prevent or substantially prevent relative rotation between the two during use.

Regardless of its exact configuration, such a locking or securement feature can help maintain the position of the sheath 140 generally fixed relative to the handle 122 and the shaft 124. This can be particularly significant when the tunneling device 120 is being guided through the anatomy to a target location. When a user wishes to separate the sheath 140 from the shaft 124 (e.g., to remove the tunneling device 120 from the anatomy), he or she can rotate the base portion 142 of the sheath 140 relative to the handle 122 so that the base portion 142 disengages the slots 184 of the protruding members 182. Consequently, the sheath 140 is no longer locked or otherwise secured to the tunneling device 120. As a result, it may be possible to rotate and/or otherwise move (e.g., slide) the sheath 140 relative to the handle 122 and the shaft 124.

Figure 9A:
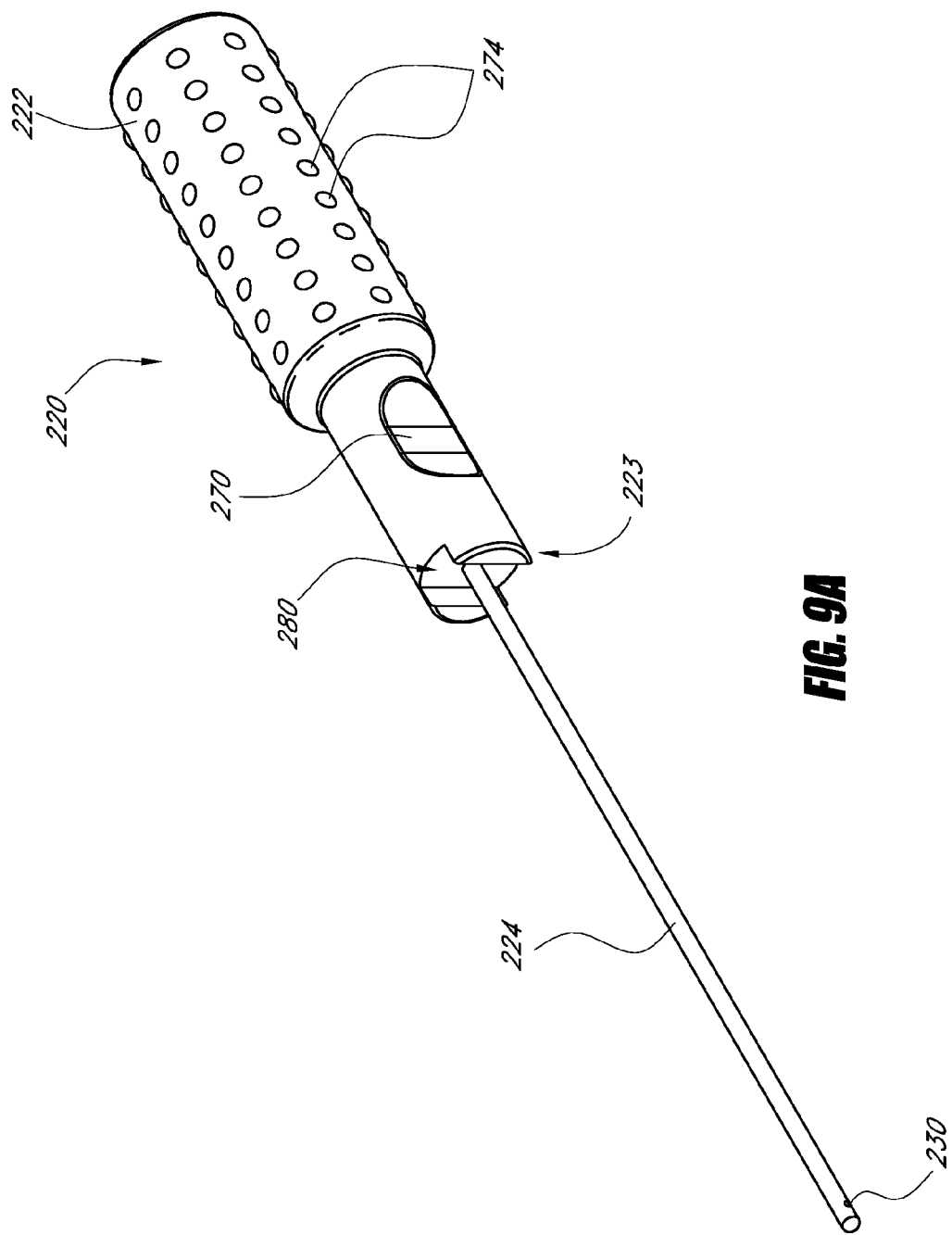
FIG. 9A is a perspective view of a tunneling device according to a different embodiment.

Another embodiment of a tunneling device 220 that is configured to generally prevent or reduce the likelihood of rotation of the sheath 240 relative to the handle portion 222 and the shaft 224 is illustrated in FIG. 9A. In the illustrated arrangement, the distal end 223 of the handle 222 comprises a groove 280, slot or other recess. As with the tunneling device 120 described herein with reference to FIGS. 7 and 8A-8C, the groove 280 can be sized, shaped and otherwise adapted to receive a base portion and/or any other area or feature of a sheath. Thus, as illustrated in FIG. 9B, once a sheath 240 is slidably inserted over the shaft 224 of the tunneling device 220, the base portion 242 of the sheath 240 can be placed within the corresponding groove 280 of the handle 222. Unlike the embodiment of FIG. 7, however, the handle 222 depicted in FIGS. 9A and 9B is not configured to secure within one or more slots or other retaining portions the sheath's base portion 242.

With continued reference to FIG. 9B, relative rotation between the sheath 240 and the tunneling device 220 is generally prevented as long as the base portion 242 of the sheath 240 is securely positioned within the groove 280. Accordingly, in some embodiments, as the tunneling device 220 is being advanced and/or maneuvered within the anatomy, the base portion 242 of the sheath 240 can be naturally retained within the groove 280. Likewise, in order to remove the sheath 240 from the shaft 224 of the tunneling device 220 and/or to permit relative rotation between the shaft 224 and the sheath 240, a user can urge the base portion 242 of the sheath 240 out of the groove 280. One or more other members or features, such as, for example, snap-fit or friction-fit arrangements, clasps, fasteners, tabs and/or the like, can be used to further ensure that the base portion 242 of the sheath remains within a groove 280 or other retaining area of the tunneling device 220 during use.

Figure 10:
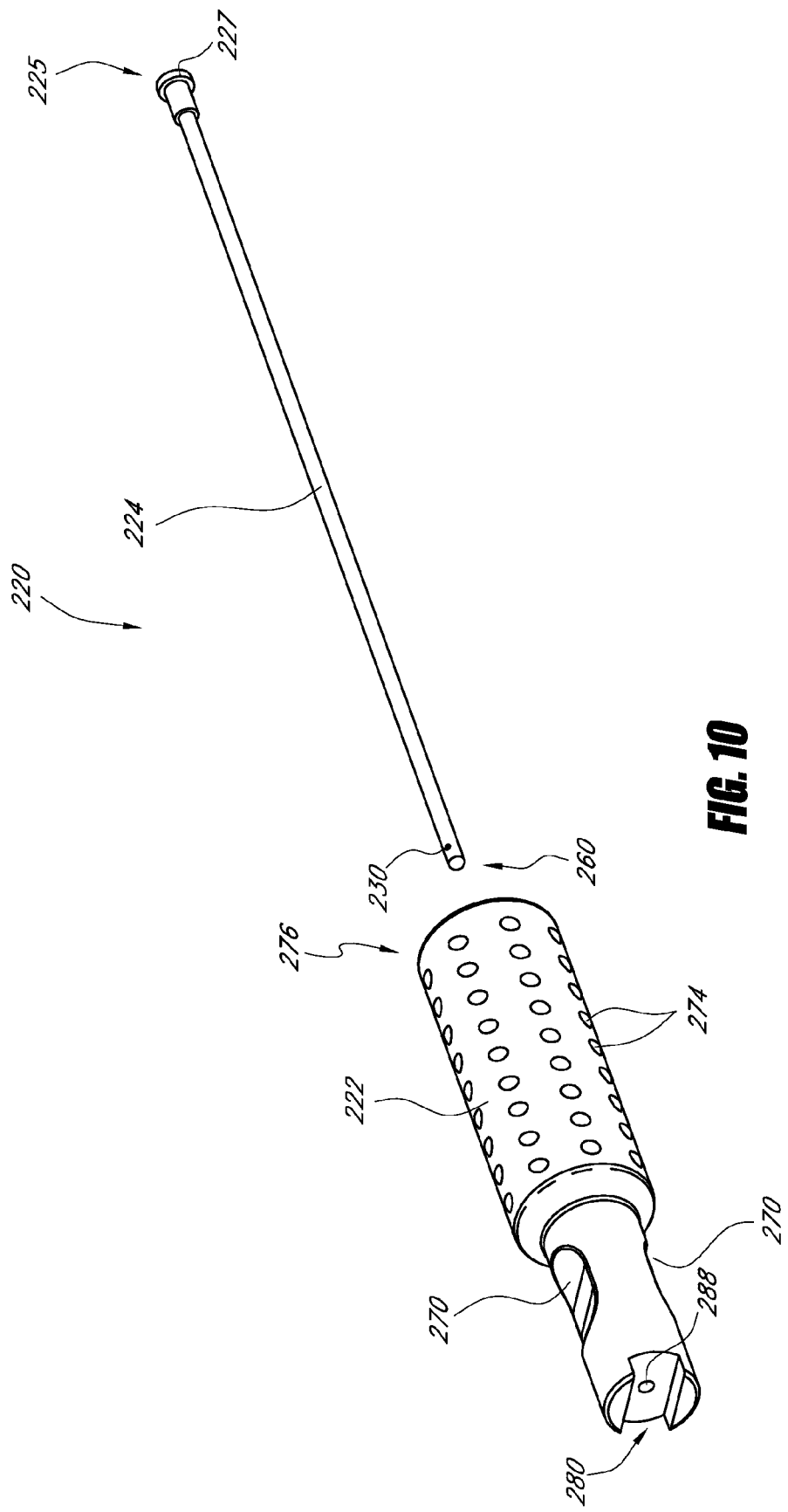
FIG. 10 is a perspective view of the tunneling device of FIG. 9A with the shaft portion removed from the handle portion.

In some embodiments, as illustrated in FIG. 10, the shaft 224 of the tunneling device 220 can be secured to the handle 222 by positioning the shaft 224 through an interior cavity or region of the handle 222. The shaft 224 can be placed into such an interior area from a proximal end of the handle 222. As shown, the distal end 260 of the shaft 224 can be routed through a corresponding opening 288 positioned at or near the groove 280 of the handle 222. A hub 225 or other enlarged area can help ensure that the proximal end of the shaft 224 remains within an interior portion of the handle 222. In one arrangement, the hub 225 comprises a flange 227 or other projecting member that is configured to engage and secure to a recess or other corresponding interior portion of the handle 222. For example, the hub 225 and an interior portion of the handle 222 can include a threaded connection, a snap connection and/or any other attachment method or device. Such a removable shaft 224 facilitates manufacturing of the device 220 and can permit a user to quickly and easily remove and/or replace a shaft during or between tunneling procedures, as desired or necessary.

Figure 11:
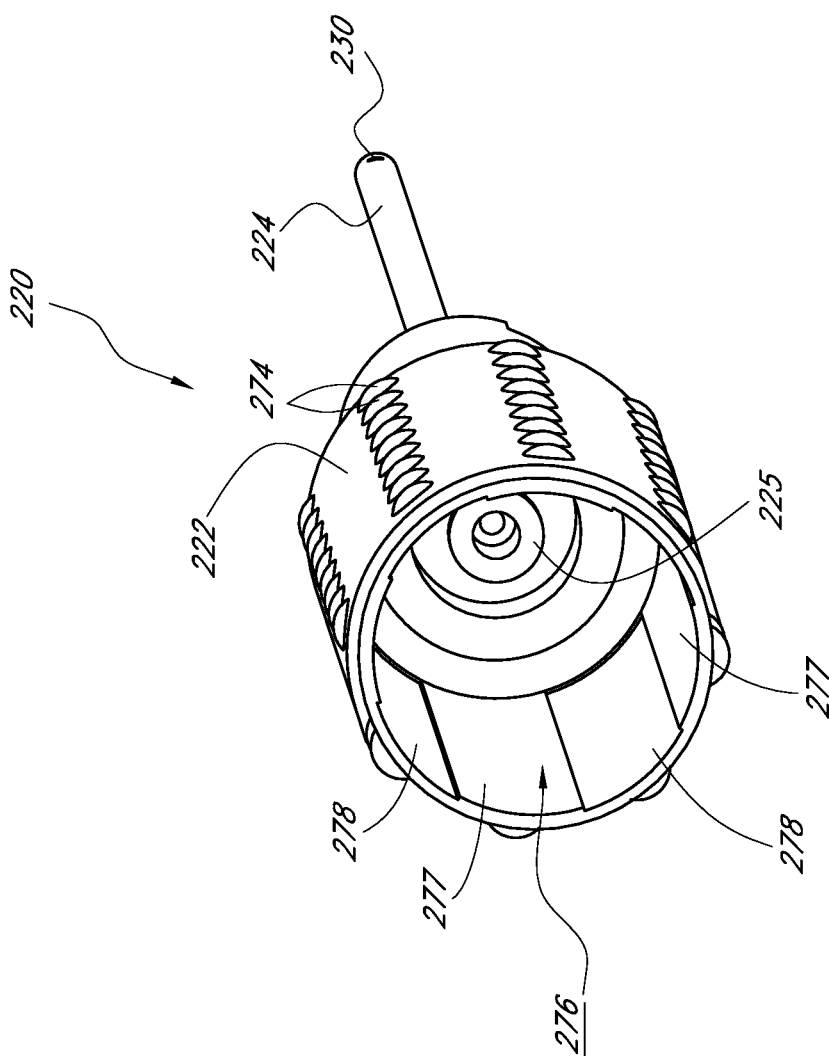
FIG. 11 is a rear perspective view of the tunneling device of FIG. 9A.

A rear perspective view of the tunneling device 220 of FIG. 10 is illustrated in FIG. 11. In some embodiments, the handle 222 of the device 220 is generally hollow or otherwise includes an internal cavity 276. In the depicted view, the hub 225 of the shaft 224 is visible along the distal end of the internal cavity 276 of the handle 222. As discussed in greater detail herein, a tunneling device can be configured to advantageously receive a syringe, a cartridge or other container, a fluid delivery device and/or any other item within an internal cavity 276 of the handle 222. Such a container or item (e.g., syringe) can be placed in fluid communication with an internal lumen and one or more openings of the shaft to selectively transfer fluids or other substances to and/or from a desired anatomical location.

With continued reference to FIG. 11, the internal cavity 276 of the handle 222 can include one or more raised surfaces 277 or other features that are shaped, sized and otherwise configured to frictionally engage an outer portion of a syringe, cartridge or other container placed therein. Grooves 278 generally positioned between adjacent raised surfaces 277 or other features can permit air or other fluids to freely exit or enter the internal cavity 276 as a syringe or other container is inserted or removed. In the illustrated arrangement, the handle 222 comprises a total of four raised surfaces 277 and four grooves 278. As shown, the raised surfaces 277 and corresponding grooves 278 can be alternatively arranged around the entire inner diameter of the internal cavity 276 in a regular, repeating manner. However, the quantity, type, size, orientation, spacing and/or other details regarding the raised surfaces 277 and grooves 278 can be varied, as desired or required.

The inclusion of grooves or other features that permit air to enter and exit the internal cavity 276 can advantageously facilitate the insertion and removal of a syringe or other container within or from a tunneling device 220. For example, as a syringe is being positioned within the internal cavity 276 of the handle 222, air situated within the internal cavity 276 can exit through the spaces generally defined between the grooves 278 and the exterior surfaces of the syringe. Likewise, when a syringe is being removed from the internal cavity 276 of the handle 222, air can enter into the internal cavity 276 to prevent a vacuum therein.

The tunneling device 220 can include one or more other ways of permitting air to move into and/or out of the internal cavity 276 when a syringe or other container is being removed and/or inserted into the handle portion 222 of the device 220. For example, the wall of the handle 222 can comprise one or more openings (not illustrated). Such openings can place the area around the exterior of the device 220 in fluid communication with the internal cavity 276 of the handle 222. Consequently, air can easily enter and/or exit the internal cavity 276 to avoid an over-pressurization or vacuum scenario.

Figure 12:
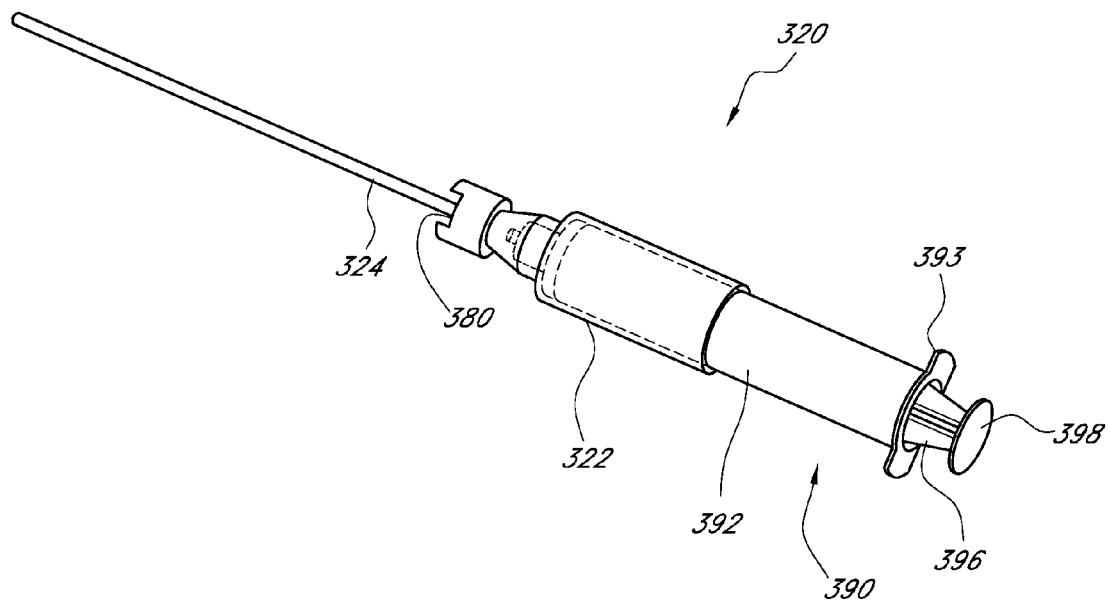
FIG. 12 is a perspective view of one embodiment of a tunneling device configured to receive a syringe within its handle portion according to one embodiment.
Figure 13:
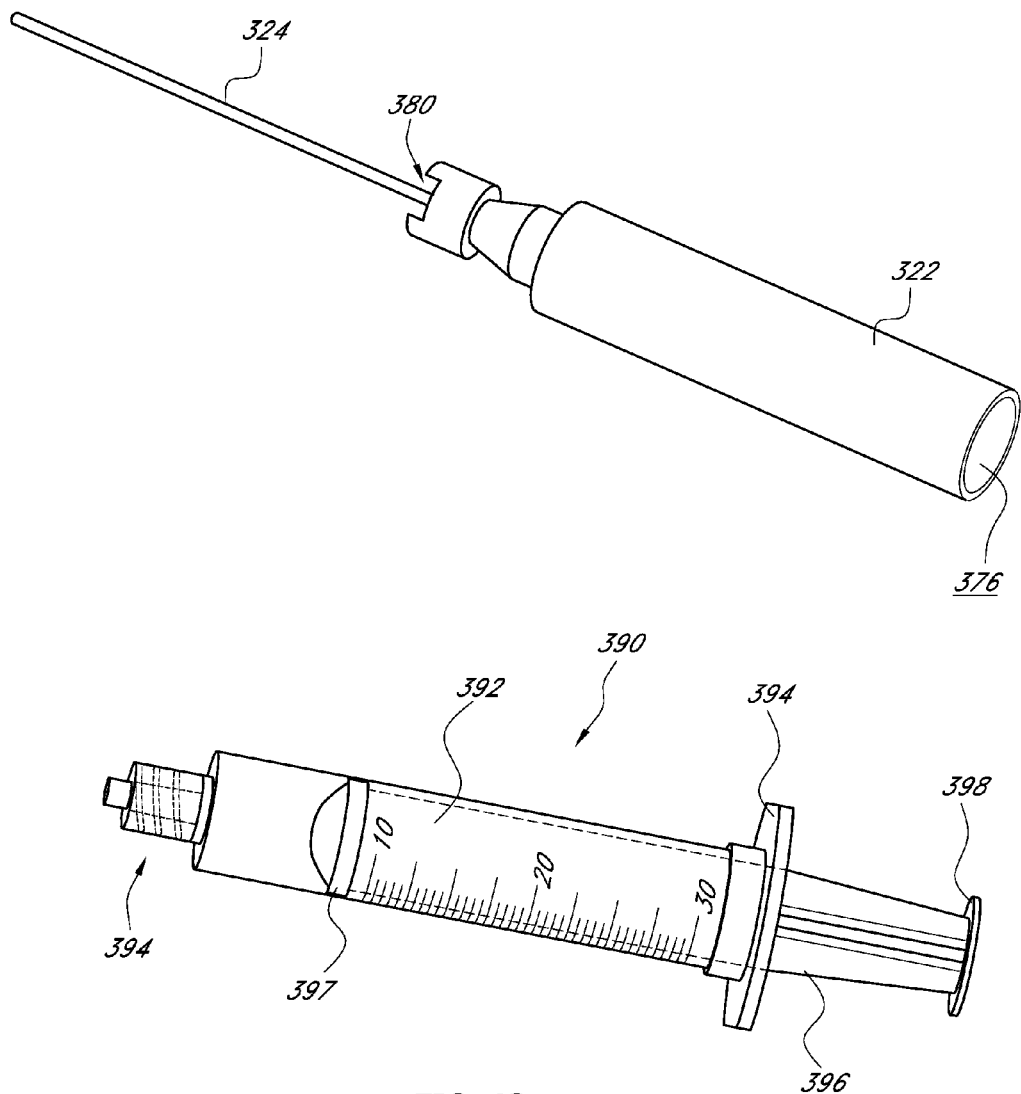
FIG. 13 is a perspective view of the tunneling device of FIG. 12 with the syringe removed from the cavity of the handle portion.

FIGS. 12 and 13 illustrate one embodiment of a tunneling device 320 configured to receive a syringe 390 or other fluid source within its handle portion 322. As with other arrangements disclosed herein, the depicted tunneling device 320 comprises a shaft 324 that can be adapted to slidably receive a sheath (not shown). It will be appreciated that the size, shape, malleability, other physical properties and/or characteristics of the shaft 324 can vary as desired or required by a particular application or use. In addition, the handle 322 can include a groove 380, recess and/or any other feature that is capable of completely or partially restricting the movement (e.g., rotation, longitudinal translation, etc.) of a sheath relative to the shaft 324 and/or the handle 322. In accordance with other embodiments disclosed herein, the groove 380 can additionally include one or more slots 184 (FIG. 8B) and/or other components to effectively lock or further restrict the movement of a sheath 340 relative to the adjacent shaft 324.

With continued reference to FIG. 13, the handle portion 322 of the tunneling device 320 can comprise a generally cylindrical shape that is adapted to securely receive a standard or non-standard syringe (e.g., 30 cc) within its internal cavity 376. In some embodiments, the interior cavity 376 includes a fitting (e.g., luer fitting, other threaded connection, etc.) and/or other attachment feature or device that is configured to engage one or more portions of a syringe 390 or other item placed within the handle 322. The tunneling device 320 can be configured to permit a syringe 390 or other item to be removably attached to and/or detached from the handle 322, shaft 324, or other portion of the tunneling device 320 (such as a proximal hub of the shaft 324, for example). For example, as illustrated in FIG. 13, the syringe 390 comprises a standard luer fitting 394 that is sized, shaped and otherwise adapted to connect to a corresponding fitting (not shown) at or near the proximal end of the handle's interior cavity 376. Alternatively, any other type of fittings, connection devices and/or features can be used to help secure the syringe 390 to the handle 322.

Accordingly, the syringe 390 can be used to transfer one or more medications (e.g., anesthetics, pain-relieving medications, etc.), other fluids or substances or the like to and/or from the lumen and openings of the shaft 324. As illustrated in FIG. 13, the syringe can comprise an outer housing 392 that is sized, shaped and configured to receive an interior plunger member 396. The plunger member 396 can be moved into and/or out of the housing 392 to selectively transfer (e.g., deliver and/or aspirate) fluids and other materials to or from the shaft 324 of the tunneling device 320. The distal end of the plunger member 396 can include a sealing member 397 (e.g., rubber stopper, gasket and/or the like) that generally forms a relatively tight seal with the interior wall of the housing 392.

Once a syringe 390 has been filled with one or more fluids and/or other substances, it may be inserted into the interior cavity 376 of the device's handle 322. As discussed, the syringe 390 can be secured to the handle 322 using a luer lock fitting and/or any other device or method (e.g., snap fit connection, friction fit connection, threaded connection, tabs, fasteners, etc.). One embodiment of a syringe 390 securely positioned within the handle 322 of tunneling device 320 is illustrated in FIG. 12. In such arrangements, the outer housing 392 of the syringe 390 can effectively extend the graspable portion of a tunneling device 320. Accordingly, users can grip one or more portions of the handle 322 and/or the outer housing 392 of the syringe 390 when manipulating the device 320.

In other embodiments, the handle 322 is sized, shaped and configured to completely or partially receive a syringe 390 or any other container or device within its interior cavity. Thus, most or all of the outer housing 392 of the syringe 390 can be covered by the handle 322 when the syringe 390 is properly attached to the tunneling device 320. For example, in one arrangement, the neck portion 393 of the syringe's outer housing 392 contacts or nearly contacts the distal end of the handle 322. In other embodiments, more or less of the syringe 390, container or other device attached to the tunneling device 320 can be exposed, as desired or required.

Once the syringe 390 or other container has been properly connected to a tunneling device 320, a user can actuate the plunger 396 (e.g., using the plunger grip 396 or any other portion or component) to selectively deliver fluids from and/or remove fluids from (e.g., aspirate) the shaft 324. As discussed herein, the shaft 324 can advantageously comprise one or more lumens and openings through which fluids and/or other substances can be transferred.

As discussed, in other embodiments, a tunneling device is adapted to receive another type of fluid container or delivery source, such as, a vial, an output line from a pump or other fluid transfer device and/or the like. Such containers or fluid sources can be advantageously placed in fluid communication with the handle (e.g., a cavity portion of the handle) and/or any other portion of the tunneling device. In some embodiments, an internal space of a container can be pressurized (e.g., by moving a plunger to decrease the volume of the internal space, by activating a compressor, etc.) in order to transfer fluids and/or other substances from the container to the lumen and openings of shaft.

Figure 14:
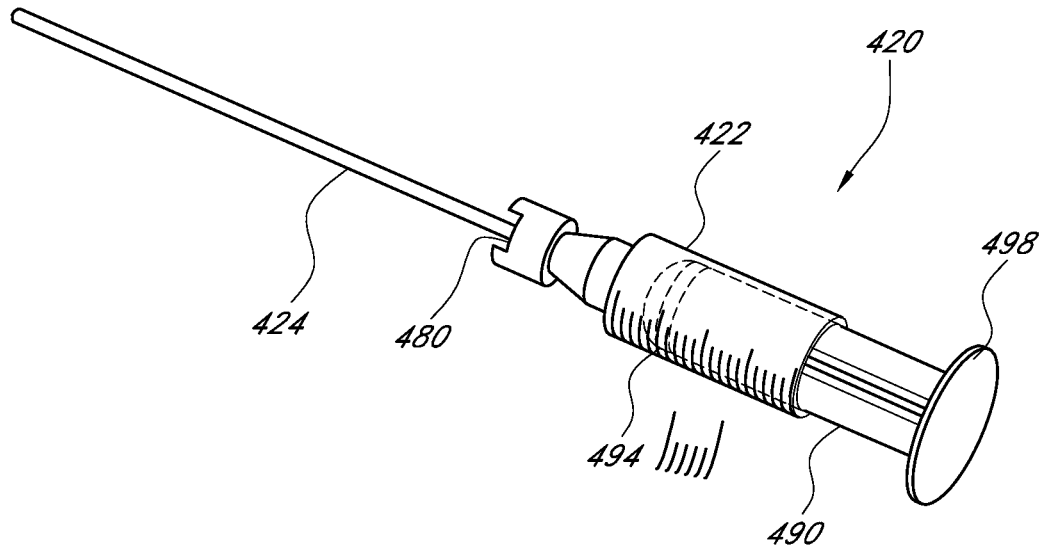
FIG. 14 is a perspective view of one embodiment of a tunneling device wherein its handle portion in integrated with a syringe.

FIG. 14 illustrates an embodiment of a tunneling device 420 having a syringe 490 integrated within the device's handle portion 422. As with the arrangement of FIGS. 12 and 13, the depicted tunneling device 420 includes a handle 422 with a generally cylindrical and hollow handle 422. Accordingly, an interior cavity of the handle 422 can be selectively placed in fluid communication with a lumen and openings of the shaft 424. Consequently, fluids and/or other substances to be delivered to the anatomy can be placed directly into the cavity of the handle 422. Alternatively, such a cavity can receive fluids and/or other materials that are aspirated from the anatomy during a particular procedure. As a result, the need to connect and/or detach a separate syringe from the handle can be eliminated in such embodiments.

With further reference to FIG. 14, a plunger member 490 can be sized, shaped and otherwise configured for direct placement within an interior cavity of the handle 422. The plunger member 490 can include a sealing member 494 (e.g., gasket, stopper, etc.) along its distal end and a grip portion 498 along its proximal end. In some embodiments the handle 422 is at least partially transparent and/or includes a transparent window or other viewable portion. This can allow a user to accurately determine the volume of fluid and/or other materials that have been delivered into an anatomy or aspirated from it. Further, in order to allow for accurate delivery (or withdrawal) of medications, other fluids and/or other materials, the handle 422 can be volumetrically graduated.

Figure 15:
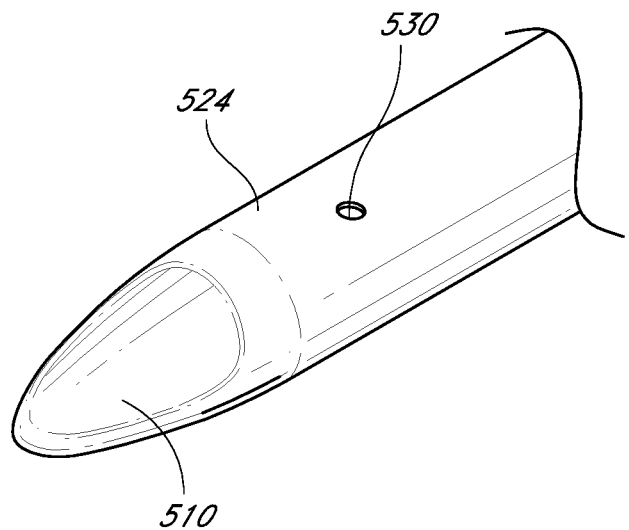
FIG. 15 is a perspective view of one embodiment of a tip for use in a tunneling device shaft.
Figure 16:
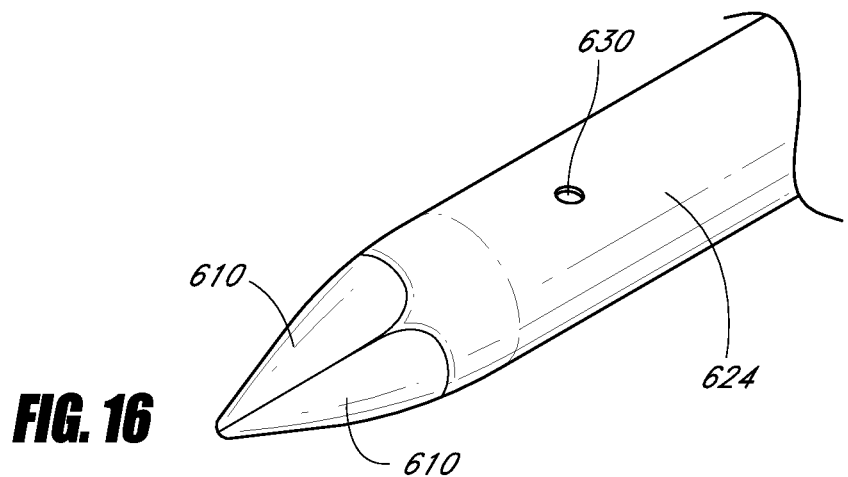
FIG. 16 is a perspective view of another embodiment of a tip for use in a tunneling device shaft.

FIGS. 15 and 16 illustrate two arrangements of shaft tip designs for use on any of the tunneling device embodiments disclosed herein. With reference to FIG. 15, the shaft 524 of a tunneling device can include one or more openings 530 (e.g., irrigation orifices), which as discussed herein, can be in fluid communication with an interior lumen (not shown) of the shaft 524. This can permit a user to selectively transfer fluids (e.g., anesthetics, other pain relieving medication, bodily fluids, etc.) to and/or from the anatomy.

As shown, the shaft 524 can also include one or more facets 510 or other areas at or near its distal end. The facets 510 can comprise a flat, curved (e.g., concave, convex, etc.), fluted and/or any other shape. In FIG. 15, the depicted arrangement comprises a total of two facets 510 situated on opposite ends and generally at the tapered distal end of the shaft 524. In some embodiments, such facets 510 give the shaft tip a generally flat screwdriver shape; however, preferably the shaft tip retains a rounded distal end between the facets 510, as shown. The use of such tapered configurations having one or more facets 510 can facilitate the insertion and advancement of a tunneling device within the anatomy, as the contoured tip shape can help reduce or minimize tissue damage. In other embodiments, the quantity, shape, size, location, spacing and/or other details of the facets 510 or other surface features or areas can vary, as desired.

As illustrated in FIG. 16, the shaft 624 can include three or more facets 610. In some arrangements, the facets 610 are located at or near a tapered, distal end of the shaft 624. In the illustrated embodiment, the shaft 624 comprises three generally equally-sized facets 610 having a tear-drop shape. The facets 610 can include a flat, substantially flat, curved (e.g., concave, convex, etc.) and/or any other shape, as desired or required. Thus, the shaft 624 of the tunneling device can be configured to resemble a trocar device. However, as discussed, the quantity, shape, size, location, spacing, orientation, curvature and/or details of the facets 610 can vary, as desired or required. As disclosed herein with reference to other embodiments, the shaft 624 can include one or more fluid openings 630 that are configured to be in fluid communication with one or more internal lumens (not shown).

As discussed, in any of the embodiments disclosed herein, the tunneling device can be configured to prevent the rotation of the sheath relative to the shaft and handle portion. This can be accomplished by placing a base and/or other portion of the sheath within a corresponding groove, recess and/or other feature of the handle of the tunneling device. In other embodiments, the handle or other portion of the tunneling device includes one or more slots or other engagement members or features that are adapted to receive corresponding portions of a sheath once the sheath is rotated or otherwise moved relative to the slots. In one embodiment, a user can secure a base portion of the sheath within the slots of the handle by rotating the sheath relative to the slots by a quarter revolution (e.g., 90°) turn. In other embodiments, the relative rotation required may be greater or less than 90°. Alternatively, one or more other methods or devices of securing a sheath to shaft of the tunneling device can be used. Regardless of the manner in which the relative movement (e.g., rotation, longitudinal translation, etc.) between the shaft and the sheath is reduced or eliminated, the process of advancing the tunneling device together with an outer sheath through soft tissues of an anatomy can be facilitated.

In any of the embodiments disclosed herein, or equivalents thereof, the tunneling device may be manufactured to be disposable or reusable. The tunneling device may be alternatively arranged so that only a portion of the device is reusable. For example, in one embodiment, the handle of the tunneling device may be reused while the shaft and other components, especially those that contact the anatomy and/or bodily fluids, are discarded after a single use.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A tunneling device for creating a path for placement of an item within an anatomy of a patient, comprising:
   an elongated shaft having a generally rounded distal end wherein said shaft comprises an interior lumen with a closed distal end that ends prior to the distal end of said shaft and at least one opening positioned proximally of said distal end of said shaft, wherein a fluid exiting the at least one opening exits proximally of said distal end of said shaft, and wherein the elongated shaft remains in the patient to introduce the fluid;
   a handle secured to said shaft and having a distal end, said handle being configured to permit a user to grasp and manipulate said tunneling device; and
   a sheath slidably positioned over a portion of said shaft, said sheath having a proximal end, said proximal end comprising a base portion;
   wherein the distal end of said handle comprises two externally visible protruding members found on the exterior surface of the distal end of said handle, the protruding members configured on opposite sides of said shaft, each of the protruding members comprising an attached portion and a free portion, the free portions being substantially perpendicular to the attached portions so as to form a slot with the distal end of the handle, wherein at least a part of the base portion is adapted to be engaged within each of the slots so as to substantially prevent relative rotation between the shaft and the sheath when the tunneling device is being manipulated within an anatomy, and wherein when engaged, the free portions provide an externally visible indicator to said user of engagement between said handle and sheath; and
   wherein said sheath is flexible and comprises an outermost exterior of the tunneling device and is configured to be selectively removed from the shaft once said tunneling device has been advanced to a desired anatomical location, such that the shaft may be removed while the sheath remains positioned at the desired anatomical location.

2. The tunneling device of claim 1, wherein the sheath comprises a catheter.

3. The tunneling device of claim 1, wherein the free portions extend in opposite directions relative to each other.

4. The tunneling device of claim 1, wherein said handle comprises an interior passageway, said opening and passageway being in fluid communication with said lumen.

5. The tunneling device of claim 4, wherein said handle comprises a fitting, said fitting being configured to place an external fluid source in fluid communication with said passageway and lumen.

6. The tunneling device of claim 5, wherein said fitting comprises a luer fitting positioned at or near a proximal end of the handle.

7. The tunneling device of claim 5, wherein said external fluid source comprises a syringe.

8. The tunneling device of claim 1, wherein said shaft is malleable so as to permit a shape of said shaft to be altered prior to use of said tunneling device.

9. The tunneling device of claim 8, wherein the shaft is malleable and may be shaped into non-linear shapes and retain these shapes during insertion of the shaft.

10. The tunneling device of claim 9, wherein the shaft may be further shaped during insertion of the tunneling device.

11. The tunneling device of claim 1, wherein the distal end of said shaft comprises at least one facet to facilitate advancement of the device through the anatomy.

12. A tunneling device for creating a path in an anatomy of a patient through which an item may be routed, comprising:
    an elongated shaft having an exterior surface and a generally rounded distal end, said shaft defining at least one interior lumen wherein the at least one interior lumen has a closed distal end and ends prior to the distal end of said shaft, wherein the elongated shaft remains in the patient to introduce the fluid;
    a handle secured to said shaft, said handle configured to permit a user to grasp and manipulate said device;
    at least one fluid opening positioned proximally of said distal end along said shaft, said opening extending from said interior lumen to said external surface of said shaft, wherein a fluid exiting the at least one fluid opening exits proximally of said distal end of said shaft;
    wherein said handle comprises an internal cavity configured to receive a fluid container, said fluid container being adapted to be in fluid communication with the interior lumen of the shaft;
    wherein a distal end of said handle comprises two externally visible protruding members found on an exterior surface of the distal end of said handle, the protruding members configured on opposite sides of said shaft, each of the protruding members comprising an attached portion and a free portion, the free portion and the attached portion forming a slot with the distal end of the handle, the free portions of the protruding members extending in opposite directions relative to each other, wherein at least a part of the base portion is adapted to be engaged within each of the slots so as to substantially prevent relative rotation between the shaft and the sheath, and wherein when engaged, the free portions provide an externally visible indicator to said user of engagement between said handle and sheath; and
    wherein said shaft is configured to be removed from said sheath, said sheath being flexible such that said sheath remains within the anatomy of the patient while the shaft is removed.

13. The tunneling device of claim 12, wherein said fluid container comprises a syringe.

14. The tunneling device of claim 13, wherein a distal end of said syringe comprises a luer fitting that is configured to be selectively attached to and removed from a corresponding fitting within the internal cavity of said handle.

15. The tunneling device of claim 12, wherein said fluid container forms a unitary structure with said handle.

16. The tunneling device of claim 12, wherein said handle is configured to directly receive a plunger member within said internal cavity, wherein movement of the plunger member into and out of said internal cavity causes fluids to be transferred to and from said interior lumen and openings.

17. The tunneling device of claim 12, further comprising a sheath configured to be slidably positioned over a portion of said shaft.

18. The tunneling device of claim 17, wherein said sheath comprises a generally snug fit with said shaft such that said sheath and said shaft can be advanced together within the anatomy.

19. The tunneling device of claim 17, wherein said sheath comprises a catheter.

20. The tunneling device of claim 12, wherein an outer surface of said fluid container generally serves as an extension of the handle to permit a user to selectively grasp both the handle and the fluid container during manipulation of the tunneling device.

21. A method of introducing a tunneling device into a body, comprising:

grasping a handle of a tunneling device, said tunneling device comprising an elongated shaft having a rounded distal end and defining at least one interior lumen wherein the at least one interior lumen has a closed distal end and ends prior to the distal end of said shaft, said tunneling device further comprising at least one fluid exit opening in fluid communication with said interior lumen positioned proximally of said distal end, wherein a fluid exiting the at least one fluid exit opening exits proximally of said distal end of said shaft;

wherein the tunneling device further comprises a sheath positioned over at least a portion of the elongated shaft;

securing the sheath to the handle of the tunneling device so as to prevent relative rotation between the sheath and the shaft during use of the tunneling device;

wherein securing the sheath to the handle comprises engaging a base portion of a proximal end of said sheath within a plurality of slots formed by two externally visible protruding members configured on opposite sides of said shaft, wherein each of the protruding members comprises an attached portion and a free portion, the free portion and the attached portion forming one of the slots with the distal end of the handle, the free portions of the protruding members extending in opposite directions relative to each other, and wherein when engaged, the free portions provide an externally visible indicator to said user of engagement between said handle and sheath;

introducing said tunneling device into the body of a patient;

advancing said tunneling device within the body;

administering the fluid through said interior lumen and into the body of the patient, wherein the elongated shaft remains in the patient to introduce the fluid; and further comprising withdrawing said shaft from said sheath, which is flexible and comprises an outermost exterior of the tunneling device, and leaving said sheath within the body while the shaft is removed.

22. The method of claim 21, wherein said handle comprises a cavity, said cavity being configured to receive and secure a syringe, said syringe being in fluid communication with said interior lumen and fluid exit opening of the shaft.

23. The method of claim 21, further comprising delivering a catheter through said sheath after withdrawal of said shaft.

24. The method of claim 21, wherein the shaft is malleable, the method further comprising altering said shaft into a non-linear shape prior to said introducing of said tunneling device into the body of the patient.

25. The method of claim 24, wherein the shaft is malleable and may be shaped into non-linear shapes and retain these shapes during insertion of the shaft.

26. The method of claim 25, wherein the shaft may be further shaped during insertion of the tunneling device.

27. The method of claim 21, wherein the sheath comprises a catheter.

\* \* \* \* \*